US005756673A

United States Patent [19]

Sonenshein et al.

[11] Patent Number: 5,756,673
[45] Date of Patent: May 26, 1998

[54] REGULATION OF SMOOTH MUSCLE CELL PROLIFERATION

[75] Inventors: Gail E. Sonenshein, Brookline; Roger Lawrence, Hull; Robert E. Bellas, Boston, all of Mass.

[73] Assignee: Trustees of Boston University, Boston, Mass.

[21] Appl. No.: 470,834

[22] Filed: Jun. 6, 1995

Related U.S. Application Data

[63] Continuation of Ser. No. 354,101, Dec. 6, 1994.
[51] Int. Cl.$^6$ .................. C07K 14/00; C07K 14/435; C07K 14/475
[52] U.S. Cl. ............................. 530/350; 514/2
[58] Field of Search ................... 536/24.1; 514/2; 530/350

[56] References Cited

U.S. PATENT DOCUMENTS

| | | | |
|---|---|---|---|
| 4,444,778 | 4/1984 | Coughlin | 424/262 |
| 4,534,967 | 8/1985 | Jacobson et al. | 424/95 |
| 4,824,436 | 4/1989 | Wolinsky | 604/53 |
| 4,945,086 | 7/1990 | Benitz et al. | 514/56 |
| 5,019,562 | 5/1991 | Folkman et al. | 514/58 |
| 5,032,679 | 7/1991 | Brandley et al. | 536/21 |
| 5,053,033 | 10/1991 | Clarke | 606/3 |
| 5,102,402 | 4/1992 | Dror et al. | 604/265 |
| 5,116,864 | 5/1992 | March et al. | 514/455 |
| 5,125,888 | 6/1992 | Howard et al. | 600/12 |
| 5,171,217 | 12/1992 | March et al. | 604/53 |
| 5,208,019 | 5/1993 | Hansson et al. | 424/85.5 |
| 5,229,493 | 7/1993 | Folkman et al. | 530/350 |
| 5,241,049 | 8/1993 | Goodman et al. | 530/350 |
| 5,242,397 | 9/1993 | Barath et al. | 604/96 |
| 5,242,692 | 9/1993 | Dialdetti et al. | 424/548 |
| 5,250,519 | 10/1993 | Conrad et al. | 514/56 |
| 5,254,342 | 10/1993 | Shen et al. | 424/401 |
| 5,268,358 | 12/1993 | Fretto | 514/12 |
| 5,270,047 | 12/1993 | Kauffman et al. | 424/422 |
| 5,271,961 | 12/1993 | Mathiowitz et al. | 427/213.31 |
| 5,280,016 | 1/1994 | Conrad et al. | 514/56 |
| 5,283,257 | 2/1994 | Gregory et al. | 514/458 |
| 5,284,868 | 2/1994 | Dell et al. | 514/454 |
| 5,288,711 | 2/1994 | Mitchell et al. | 514/56 |
| 5,298,018 | 3/1994 | Narciso, Jr. | 604/21 |
| 5,302,168 | 4/1994 | Hoss | 600/3 |
| 5,304,121 | 4/1994 | Sahatjan | 604/53 |
| 5,304,473 | 4/1994 | Belagaje et al. | 435/69.7 |
| 5,304,541 | 4/1994 | Purchio et al. | 514/12 |
| 5,308,622 | 5/1994 | Casscells et al. | 424/422 |
| 5,314,688 | 5/1994 | Kauffman et al. | 424/423 |
| 5,322,678 | 6/1994 | Morgan, Jr. et al. | 424/1.53 |
| 5,324,655 | 6/1994 | Kriegler et al. | 435/240.2 |
| 5,326,559 | 7/1994 | Miller | 424/85.2 |
| 5,328,695 | 7/1994 | Lucas et al. | 424/426 |

OTHER PUBLICATIONS

"Probucol Decreases Neointimal Formation in a Swine Model of Coronary Artery Ballon Injury". Joel E. Schneider, MD et al., Circulation, vol. 88, No. 2, Aug. 1993, pp. 628–637.

"Probucol inhibits neointimal thickening and macrophase accumulation after bellon injury in the cholesterl–fed rabbit", Gordon A.A. Ferns et al., Proc. Natl. Acad. Sci. USA, vol. 89, pp. 11312–11316, Dec. 1992.

"Probucol attenuates the development of aortic atherosclerosis in cholesterol–fed rabbits", Alan Daugherty, et al., B. J. Pharmacol, (1989), vol. 98, pp. 612–618.

"NF–kB and Rel: Participants in a Multiform Transcriptional Regulatory System", Mariagrazia Grilli et al., International Review of Cytology, vol. 143, pp. 2–62.C.F.

"The inducible transcription factor NF–kB: structure–function relationship of its protein subunits", S. Grimm et al., Bio Chem J., pp. 297–308.

"The Antioxidant Butylated Hydroxytoluene Protects Against Atherosclerosis", Ingemar Bjorkhem et al., Arteriosclerois and Thrombosis, vol. 11, No. 1, Jan./Feb. 1991.

"Antioxidant Treatment Inhibits the Development of Intimal Thickening after Balloon Injury of the Aorta in Hypercholesterolemic Rabbits", Anna Freyschuss et al., J. Clin. Invest, vol. 91, Apr. 1993, pp. 1282–1288.

"Vascular Smooth Muscle Cell Express a Constitutive NF–kB–like Activity", Roger Lawrence et al., The Journal of Biological Chemistry, Vo. 269, No. 46, Issue of Nov. 18, pp. 28913–28918, 1994.

"Collagen Synthesis by Human Intestinal Smooth Muscle Cells in Culture", Martin F. Graham et al., Gastroenterology 1987, vol. 92, pp. 400–405.

"The p50 subunit of NF–kB associates with the NF–IL6 transcription factor", Kenneth P. LeClair et al., Proc. Natl. Acad. Sci. USA, vol. 89, pp. 8145–8149, Sep. 1992.

(List continued on next page.)

*Primary Examiner*—Marianne P. Allen
*Assistant Examiner*—Stephen Gucker
*Attorney, Agent, or Firm*—Baker & Botts, L.L.P.; James Remenick

[57] ABSTRACT

This invention relates to agents that regulate the proliferation of cells such as smooth muscle cells. Proliferation of smooth muscle cells may be increased or decreased by affecting the activity or concentration of a transcription factor. The factor comprises two domains of about 50 kD and about 70 kD which together have an approximate molecular weight of 120 kD and specifically binds to the nucleic acid sequence 5'-GGGTTTTCCCC-3' (SEQ ID NO 2). This factor represents a novel member of the family of rel-related factors. This invention also relates to methods for the treatment and prevention of diseases and disorders associated with proliferation of smooth muscle cells such as arteriosclerosis, fibrosis and wound healing, which involve regulation of the smooth muscle cell transcription factor. The invention further relates to purified transcription factor, to pharmaceutical compositions containing transcription factor or inhibitors or inducers of the transcription factor, to nucleic acid sequences which code for the subunits of the factor, and to recombinant cells transformed with these sequences. Novel rel-related factors can also be used to regulate gene expression and the proliferation of organisms such as cells and viruses which may contain rel-related binding elements.

6 Claims, 12 Drawing Sheets

OTHER PUBLICATIONS

"In Vitro Effects of Pentoxifylline on Smooth Muscle Cell Migration and Blood Monocyte Production of Chemotactic Activity for Smooth Muscle Cell: Potential Therapeutic Benefit in the Adult Respiratory Distress Syndrome", Anne Kullmann et al., American Journal of Respiratory Cell and Molecular Biology vol. 8, 1993, pp. 83–88.

"Stricture Formation Pathophysiologic and Therapeutic Concepts", Martin F. Graham, pp. 323–335.

"Biology of Uterine Myomas and Myometrium In Vitro", Mitchell S. Rein M.D. et al., Seminars in Reproductive Endocrinology, vol. 10, No. 4, Nov. 1992, pp. 310–319.

"The Alimentary Canal", Martin F. Graham, M.D. et al., Repair of Specific Tissues, pp. 433–449.

"NF–kB p100 Is One of the High–Molecular–Weight Proteins Complexed with the v–Rel Oncoprotein in Transformed Chicken Spleen Cells", Journal of Virology, Dec. 1993, pp. 7612–7617.

Grimm et al., *Biochem J.*, vol. 290, pp. 297–308, 1993.

SMC

WEHI 231

REGULATION OF SMOOTH MUSCLE CELL PROLIFERATION

This application is a continuation of application Ser. No. 08/354,101, filed Dec. 6, 1994.

RIGHTS IN THE INVENTION

This invention was made with United States Government support under grants HL13262, CA36355 and AG00115, each from the National Institutes of Health, and the United States Government has certain rights in the invention.

BACKGROUND

1. Field of the Invention

This invention relates to methods for controlling the proliferation of smooth muscle cells including vascular smooth muscle cells. Proliferation can be inhibited by treatment of smooth muscle cells with agents that inactivate a novel transcription factor, a representative member of a new class of rel-related factors. Stimulating the activity of this same factor can induce smooth muscle cells to multiply and proliferate. The invention also relates to purified smooth muscle cell transcription factor, to compositions containing purified transcription factor or transcription factor inhibitors and inducers, and to methods for the treatment of diseases and disorders associated with cell proliferation and the activity of members of this new class of transcription factors.

2. Description of the Background

Arteries are divided into three distinct categories based on their overall size. Large arteries comprise the elastic arteries such as the aorta, the innominate, the subclavian, the beginning of the common carotid and the origins of the pulmonary arteries. Medium sized arteries comprise the muscular arteries and, unlike the larger arteries, have fairly well-defined, layered walls. The smaller arteries include the arterioles and those vessels with an inner diameter of less than 0.2 mm. Regardless of size, each type of artery has a similar structure comprising an outer tunica adventitia, a media tunica adventitia, and an inner tunica intima. The tunica adventitia is relatively thick in the larger sized arteries and contains connective tissue in which elastic fibers, nutrient vessels (*vasa vasorum*) and nerves can be found. The tunica media is the muscular layer. It is rich in elastic tissues, especially in the larger arteries, and predominantly composed of circular or spiral smooth muscle cells (SMCs) arranged in concentric layers. The outer limit of this layer is marked with an external elastic membrane which is less well developed than the corresponding internal membrane.

The medium-sized arteries are principally the muscular arteries and the vessels sometimes referred to as the distributor arteries. These vessels permeate the muscles and organs of the body and have fairly well-defined cellular layers. The tunica adventitia of medium sized arteries is a defined layer of connective tissue in which elastic and nerve fibers are dispersed reflecting the role these vessels play in the autonomic regulation of blood flow. Small arteries have a progressive loss of external elastic membrane, such that the definitions between the layers of cells are lost. As vessel size approaches the arterioles, vessel walls comprise an endothelial lining of subendothelial connective tissue, a layer of muscular media and a small collagenous adventitia. Despite their small size, arterioles are richly supplied with nervous connections to the autonomic system and constitute the majority site of autonomic control of vascular blood flow. In this capacity, the smaller arteries and arterioles bear the brunt of elevations of blood pressure by alterations in their structure.

The main components of the vascular wall play important roles in all types of vascular pathologies. The single layer of continuous endothelium lining arteries and veins forms a unique thrombo-resistant layer between blood and potentially thrombogenic subendothelial tissues. The integrity of this layer is fundamental for maintaining normal structure and function of the entire vessel wall. Endothelial injury may be, in part, responsible for the initiation of atherosclerosis and the vascular lesions produced by hypertension.

Vascular SMCs have recently been demonstrated to possess a great many functions. These cells, rather than the fibroblasts, are responsible for intimal collagenization typically found in atherosclerosis. SMCs, in addition to having an established role in vasoconstriction and dilation, are capable of synthesizing various types of collagens, elastins and proteoglycans. Cells migrate to sites of injury, proliferate and further respond to that injury by secreting a large variety of substances. SMCs also have receptors for low-density lipoproteins as well as enzymes that regulate intracellular cholesterol metabolism. Although not normally phagocytic, SMCs can be stimulated to perform pinocytosis and phagocytosis and to develop a variety of hydrolytic enzymes. These processes may be important in lipid accumulation in vessel walls during atherosclerosis.

Vessels may be damaged due to direct injury or disease and are, of course, also affected by lesions of surrounding tissues which may also be caused by injury or disease. All vascular diseases are similar in that they damage the vessel walls, leading to dilation or rupture, narrow the lumina of the vessel producing ischemia, or damage the endothelial lining provoking intravascular thrombosis. Vascular disorders include varicose veins, which is more debilitating than life-threatening, phlebothrombosis which can lead to death through embolism, congenital anomalies such as arteriovenous fistula and aneurysm, and a wide variety of tumors and other neoplasms.

One prevalent and clinically significant vessel disease is arteriosclerosis. In time, this disorder, to some degree, affects nearly every individual. Arteriosclerosis quite literally means, hardening of the arteries. This disorder more accurately refers to a group of disorders that have a common thickening and loss of elasticity of arterial walls. The three distinct morphologies, characterized by formation of fibro-fatty intimal plaques (atheromas) and all referred to as atherosclerosis, include Monckeberg's medical calcific sclerosis, characterized by calcification of the media of muscular arteries, and atherosclerosis, characterized by proliferation or hyaline thickening of the walls of the small arteries and arterioles. More than one of these disorders is typically found in a single individual.

SMCs, the cells responsible for the production of connective tissue, the bulk of the vessel wall and to a large extent vessel wall integrity, demonstrate increased migration and proliferation within the intima of diseased and injured arteries. These cells can be characterized morphologically as unstriated and spindle-shaped with centrally located nuclei. Typically, smooth muscle cells are bound in sheets and are found in the internal organs including the uterus and heart, hair follicles and, of course, blood vessels. Proliferation of SMCs within vessels results in excess connective tissue deposition and the development of atherosclerotic fibrous plaques that block veins and arteries producing pathologies such as atherosclerosis, hypertension, ischemic injury, stroke, and myocardial infarction. The formation of plaques within vessels leads to partial blockage or occlusion of blood flow, also referred to as stenosis, to major arteries and tissues. Proliferation of SMCs into and along the vessel walls, to a large extent, is responsible for plaque formation. Pathology is not limited to arteries, but can also occur in any vessel including veins and arterioles.

Injury of the vascular endothelium is considered by most to be the initiating event in the development of stenosis. Mechanical injuries such as angioplasty, vascular surgery, transplantation surgery and other invasive processes that disrupt vascular integrity, lead to the proliferation of smooth muscle cells in vessels and arteries. Stenosis is also induced biologically by stresses, which may be internally or externally derived, that injure the vascular endothelium.

Current treatment regimes for stenosis or occluded vessels includes mechanical interventions, however, these techniques also serve to exacerbate the injury, precipitating a new bout of SMC proliferation. For example, occluded arteries are often treated with balloon angioplasty which involves the mechanical dilation of a vessel with an inflatable catheter. The effectiveness of this surgery is limited because the treatment itself damages the vessel thereby inducing proliferation of SMCs and re-occlusion or restenosis of the vessel. Approximately 30–40% of patients treated by balloon angioplasty experience restenosis within one year of surgery.

A number of agents which affect cell proliferation have been tested as pharmacological treatments for stenosis and restenosis in an attempt to slow or inhibit proliferation of SMCs. These compositions have included heparin, coumarin, aspirin, fish oils, calcium antagonists, steroids, prostacyclin, rapamycin, dipryidamole, ultraviolet irradiation, gamma (γ)-interferon, serotonin inhibitors, methotextrate and mycophenolic acid, either alone or in various combinations. For example, heparin is commonly used following coronary angioplasty to reduce the incidence of acute thrombotic occlusion and reduce the proliferation of SMCs (Guyton et al., Circ. Res. 46:625, 1980). These activities were demonstrated in vitro and confirmed in vivo in experiments on rat arterial SMC proliferation after balloon catheter injury (Gordon et al., Circulation 76:213, 1987). Wai et al. determined that a hybrid protein consisting of the ribosome inhibitor, saponin, fused to basic fibroblast growth factor (FGF), killed proliferating FGF-receptor expressing SMCs, but not quiescent receptor negative cells (Wai et al., Circulation 82:208, 1990). This same hybrid protein also inhibited intimal thickening following vascular injury.

Acetylsalicylic acid pre-treatment has been shown to reduce platelet accumulation in patients who have undergone coronary angioplasty (Cunningham et al., Radiology 151:487, 1984). A placebo controlled study in 376 patients demonstrated that while an aspirin-dipyridamine, antiplatelet regimen before and after percutaneous transluminal coronary angioplasty did not reduce the six-month rate of restenosis after successful coronary angioplasty, it markedly reduced the incidence of transmural myocardial infarction during or soon after percutaneous transluminal coronary angioplasty (Schwartz et al., N. Engl. J. Med. 318:1714, 1988).

Agents that interfere with the action of certain cytokines have also been tested for their effect on stenosis. For example, U.S. Pat. No. 5,268,358 is directed to the use of peptides that block the binding of platelet derived growth factors to their receptors. U.S. Pat. No. 5,304,541 is directed to chimeric transforming growth factor-beta (TGF-β) peptides which block cell proliferation. U.S. Pat. No. 5,308,622 is directed to conjugates comprising fibroblastic growth factor (FGF) and cytotoxic agents. U.S. Pat. No. 5,326,559 is directed to interleukin-2 targeted molecules. Although promising, many of these agents and compositions have known and serious side effects and, consequently, limited effectiveness. Each of these U.S. patents is hereby specifically incorporated by reference.

Successful treatment with pharmaceuticals generally requires delivery of the active agent to the site of the injury or the site responsible for the injury. Systemic delivery can involve enteral or parenteral routes of administration. Oral ingestion is the most common method of drug administration and also the safest. Disadvantages include the inability of certain compositions or agents to be absorbed through the gastrointestinal mucosa and destruction by the low gastric pH and enzymes present in the gastrointestinal tract. Drugs which are administered in this manner also often metabolize before they gain access to the blood stream and have an opportunity to produce any sort of beneficial effect.

Parenteral administration includes, for example, topical application to dermal tissues, pulmonary absorption (U.S. Pat. No. 5,241,049), and direct injection into the blood stream or some other site of the body, thereby avoiding the harsh environment of the gastrointestinal tract. Although topical applications are generally safe, direct injections carry a number of significant risks. Injections necessarily create a hole in the outer integument of the body providing an entrance for bacteria, virus particles and toxic substances. Consequently, aseptic conditions must be maintained for all types of injections including intravenous, subcutaneous and intramuscular.

Local delivery of a pharmaceutical agent is becoming increasingly popular and possible. Proteins have been delivered to site specific locations in the body by implanting biodegradable polymer matrices containing the pharmaceutical as described in U.S. Pat. Nos. 5,328,695 and 5,271,961. As the polymer degrades, the resulting degraded components, which are safe and non-toxic, are easily absorbed or eliminated by the body. More importantly, the released agent has an opportunity to perform its intended function before being inactivated. This method is especially useful for delivery of agents with short half-lives which would be otherwise ineffective even if they were able to pass through the gastric mucosa. Other somewhat similar methods include magnetic release of agents (U.S. Pat. No. 5,125,888), fusion to conjugates capable of rapid absorption into desired cells (U.S. Pat. Nos. 5,324,655 and 5,254,342), and charge modification of the active component (U.S. Pat. No. 5,322,678). Each of these U.S. patents is hereby specifically incorporated by reference.

Local delivery has also been achieved with the use of catheters (U.S. Pat. No. 4,636,195), stents (U.S. Pat. No. 5,304,121), coatings on balloon catheters (U.S. Pat. No. 5,102,402), direct injection of the agent formulated with a biodegradable polymer (U.S. Pat. No. 5,171,217), and hydrogel polymer/agent coatings on catheters. These antithrombogenic and anti-proliferative agents have demonstrated limited successes.

Cell proliferation in stenosis results, at least in part, from the actions of a variety of growth factors and cytokines. These include platelet derived growth factor (PDGF), epidermal growth factor (EGF), fibroblast growth factor (FGF), transforming growth factor (TGF), and a variety of interleukins (IL-1 and IL-2). One of the nuclear factors found associated with cells is the transcription factor NF-κB, a member of the rel-family of factors. NF-κB was first identified as an activity that specifically retarded the mobility of DNA fragments containing the decameric sequence 5'-GGGACTTTCC-3' (SEQ ID NO 1) (R. Sen et al., Cell 46:705–16, 1986). This sequence was identified as a B cell-specific binding element in the kappa (κ) light chain immunoglobulin gene enhancer (R. Sen et al., Cell 47:921–28, 1986). NF-κB binding to this element was induced during pre-B to B cell differentiation in association with the activation of κ light chain gene transcription. HIV-1 LTR contains two NF-κB elements that are important for transcription of this promoter (G. Nabel et al., Nature 326:711–13, 1987).

The presence of NF-κB protein was found to be fairly ubiquitous in many different cell types. In most cells this protein it is sequestered in the cytoplasm with an inhibitor protein referred to as IκB (P. A. Baeuerle et al., Science 242:540–46, 1988). Activation and nuclear localization can be induced in these cells by several agents. Activating agents include phorbol ester, IL-1, TNF-α, ultraviolet light, and serum, as well as infection by a number of viruses, including the human T-cell leukemia virus type I and Epstein-Barr viruses. Activation involves post-translational events, including inactivation and rapid degradation of IκB (K. Brown et al., Proc. Natl. Acad. Sci. USA 90:2532–36, 1993).

In addition to being required for activation of the κ light chain gene, NF-κB has been implicated in control of transcription of a number of cellular genes involved in immune and inflammatory responses, growth and adhesion (M. Grilli et al., Int. Rev. Cytol. 143:1–62, 1993). Some of these genes encode interleukins or their receptors, such as IL-2, IL-2RαIL-6, IL-8, class I MHC, GM-CSF and TNF-β, the SAA acute phase response gene, β-interferon, gro, and V-CAM-I. The c-myc oncogene contains two NF-κB binding elements called the upstream regulatory element (URE) and the internal regulatory element (IRE) (M. P. Duyao et al., Proc. Natl. Acad. Sci. USA 87:4727–31, 1990; D. J. Kessler et al., Oncogene 7:2447–53, 1992). Both sites have been shown to be required for normal activation of c-myc expression by NF-κB. NF-κB is also involved in the control of the expression of receptors, adhesion molecules and components of the cytoskeleton.

Biochemical characterization of classical NF-κB demonstrated that it is a heterodimer composed of a 50 kD (p50) subunit and a 65 kD (p65) subunit (S. Ghosh et al., Cell 62:1019–29, 1990; M. Kieran et al., Cell 62:1007–18, 1990; S. Ruben et al., Science 251:490–93, 1991). Cloning and sequencing of p50 and p65 led to the discovery that these factors are members of a larger family of proteins that includes the rel oncoproteins and the Drosophila dorsal gene products (M. Grilli et al., Internat'l Rev. Cytol. 143:1–62, 1993). The rel-related family includes p50, p65, p52 (V. Bours et al., Mol. Cell. Biol. 12:685–95, 1992). c-rel, v-rel and rel-B (R. P. Ryseck et al., Mol. Cell. Biol. 12:674–84, 1992). Rel-related family members have been shown to regulate gene expression for a number viruses including cytomegalovirus (CMV), and been recently implicated in the formation of atherosclerotic plaques (P. A. Baeuerle, Biochem. Biophys. Acta 1072:63–80, 1991; R. Ross, Nature 362:801–08, 1993), and to be involved with proliferation and restenosis (E. Speir et al., Sci. 265:391–94, 1994).

Rel-related factors generally bind to DNA as dimers (M. B. Urban et al., EMBO J. 10:1817–25, 1992). The p65 subunit, which binds to the 3' side of the binding element, contains a potent transcription activation domain (M. L. Schmitz et al., EMBO J. 10:3805–17, 1991). Transfections of vector expressing both p50 and p65, or p65 alone activate transcription of the c-myc promoter (F. La Rosa et al., Mol. Cell. Biol. 14:1039–44, 1994). In contrast, the p50 subunit alone is unable to activate transcription in vivo or activates only weakly in most cell types. c-rel, another Rel-related protein which appears to function in an element specific fashion, activates transcription moderately (T. -H. Tan et al., Mol. Cell. Biol. 12:4067–75, 1992; P. McDonell et al., Oncogene 7:163–170, 1992), whereas rel B significantly activates transcription (P. Dobrzanski et al., Mol. Cell. Biol. 13:1572–82, 1993).

Constitutive activity of this family of factors was previously thought to be restricted to hematopoietic lineage cells such as mature B cells, thymocytes and macrophages (M. J. Lenardo et al., Cell 58:227–31, 1989; M. Korner et al., Biochem. Biophys. Res. Commun. 181:80–86, 1991). However, activity of rel-related factors has been reported recently in cells of neural origin (C. Kaltschmidt et al., Mol. Cell. Biol. 14:3981–3992, 1994), and a novel inducible factor was identified in the liver (M. Tewari et al., Mol. Cell. Biol. 12:2898–2908, 1992).

SUMMARY OF THE INVENTION

The present invention overcomes the problems and disadvantages associated with current strategies and designs and provides compositions and methods for the treatment of diseases and disorders associated with smooth muscle cell proliferation.

One embodiment of the invention is directed to methods for regulating the proliferation of smooth muscle cells. According to the invention, an agent is provided that regulates the activity of a smooth muscle cell transcription factor (SMC-TF). This factor controls SMC proliferation and is composed of at least two different subunits. These subunits have molecular weights of about 50 kD and about 70 kD, with a combined molecular weight of approximately 120 kD, and together specifically bind to a double-stranded nucleic acid comprising the sequence 5'-GGGTTTTCCCC-3' (SEQ ID NO 2). An effective amount of the agent is administered to smooth muscle cells in culture or in a patient and SMC proliferation is increased or decreased as desired. Agents which stimulate SMC proliferation include increased concentrations of the factor, a related factor or active portions of these factors. Agents which decrease SMC proliferation include anti-oxidants, natural and synthetic nucleic acids such as anti-sense oligonucleotides and double-stranded oligonucleotides containing a sequence of the factor binding site, antibodies, cytokines, inhibitors of rel-like factors, dominant negative mutants of, for example, p50, proteins such as IκB, IκB-α (MAD-3), IκB-β and IκB-γ, and derivatives and combinations of these agents.

Another embodiment of the invention is directed to methods for treating or preventing arteriosclerosis. An effective amount of an agent which inhibits the activity of a smooth muscle cell transcription factor is administered to a patient. Administration may be periodic or continuous as desired for the prevention or treatment of arteriosclerosis in humans and other mammals.

Another embodiment of the invention is directed to methods for treating or preventing fibrosis in a patient. An agent is provided which inhibits the activity of a smooth muscle cell transcription factor. An effective amount of this agent is administered to a patient such as a human or another mammal. Examples of the different types of fibrotic disorders which can be controlled include inflammatory diseases such as Crohn's disease and other bowel disorders, adult respiratory distress syndrome, uterine fibroids, pulmonary fibrosis, cardiac fibrosis, arteriosclerosis and many of the fibroproliferative diseases.

Another embodiment of the invention is directed to methods to promote healing of damaged tissue in a patient. An effective amount of a SMC-TF, an SMC-TF-like factor, a portion of SMC-TF or an SMC-TF-like factor, or another agent which increases SMC-TF activity, is administered to the patient to stimulate the proliferation of smooth muscle cells. An effective amount of this factor is that amount which increases SMC proliferation and promotes healing of damaged tissue.

Another embodiment of the invention is directed to a purified transcription factor having two different subunits of about 50 kD and about 70 kD, with a combined molecular weight of approximately 120 kD, that specifically binds to a double-stranded nucleic acid comprising the sequence 5'-GGGTTTTCCCC-3' (SEQ ID NO 2). This factor is constitutively expressed in human and other mammalian derived SMCs and also binds to a number of other elements of the rel-family of sequences. Polyclonal and monoclonal antibodies can be generated which specifically bind to the factor or to subunits of the factor.

Another embodiment of the invention is directed to factors related to SMC-TF, the SMC-TF-like factors, that regulate the proliferation of the cells in which they may be expressed and/or biological organisms within those cells such as viruses. These factors bind to one or more of the rel-binding sites and can be inhibited or activated by agents which effect the activity of members of the rel-family of proteins. SMC-TF-like factors are comprised of at least two different subunits with approximate molecular weights of between about 40–60 kD and between about 60–80 kD, and have a combined molecular weight of between about 90 kD to about 150 kD.

Another embodiment of the invention is directed to a pharmaceutical composition comprising a SMC-TF or a SMC-TF-like factor, or an agent which regulates the activity of the SMC-TF or the SMC-TF-like factor, and a pharmaceutically acceptable carrier. The carrier may be water, oils, fatty acids, alcohols, salts, saccharides, polysaccharides, celluloses, starches or combinations thereof.

Another embodiment of the invention is directed to nucleic acid sequences that code for two subunits of a protein factor with approximate molecular weights of 50 kD and 70 kD with a combined molecular weight of approximately 120 kD, and that specifically binds to a double-stranded nucleic acid containing the sequence 5'-GGGTTTTCCCC-3' (SEQ ID NO 2). Subunit sequences may be separate or combined, for example, as a contiguous sequence on a vector such as a plasmid, cosmid, phage or viral vector.

Another embodiment of the invention is directed to a cell transformed with the nucleic acid sequence that codes for a SMC-TF, a SMC-TF related factor or subunits or portions of these factors. Recombinant cells may be prokaryotic such as bacterial cells or eukaryotic such as mammalian, yeast or insect cells.

Another embodiment of the invention is directed to methods for regulating the expression of genes which contain a SMC-TF regulatory element. By controlling the activity of the SMC-TF, gene expression can be regulated. Genes which contain a SMC-TF regulatory element include genes possessing an enhancer element, genes which encode extracellular matrix proteins, immunoglobulins and cytolines, and recombinant genes.

Another embodiment of the invention is directed to methods for controlling the activities of biological organisms, such as cells and viruses within cells, by regulating the activity of a SMC-TF or SMC-TF-like factor. Biological organisms which can be controlled include cells such as SMCs, and viruses such as cytomegalovirus and other herpes-type viruses, retroviruses such as HIV, and certain of the human papilloma viruses. Control over proliferative activities of cells and viruses can also provide an effective treatment or prevention against many diseases and disorders which are either directly or indirectly related to the activities of such cells and viruses.

Other embodiments and advantages of the invention are set forth, in part, in the description which follows and, in part, will be obvious from this description and may be learned from the practice of the invention.

DESCRIPTION OF THE INVENTION

Figure 1A:
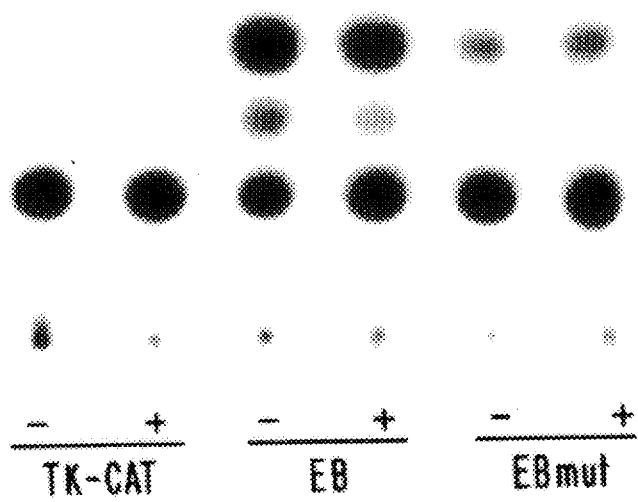
FIGS. 1A and B SMC cultures express a constitutive rel-related activity that is unresponsive to serum as determined in CAT assays using (a) E8 and E8mut constructs and (b) κB and κBmut constructs.

As embodied and broadly described herein, the present invention is directed to agents which regulate the proliferation of SMCs such as purified SMC-TFs and SMC-TF-like factors, compositions containing regulatory agents or SMC-TFs, and to methods for the treatment or prevention of diseases and disorders associated with the proliferation of SMCs, the proliferation of other cells expressing SMC-TF or SMC-TF-like factors, and the proliferation of viruses which may also be regulated by these transcription factors.

One embodiment of the invention is directed to a purified smooth muscle cell transcription factor, SMC-TF. This factor is a member of a group or family of factors, all of which are members of the larger group of factors referred to as the rel-family of proteins. As determined by non-denaturing polyacrylamide gel electrophoresis, SMC-TF comprises at least two different subunits with molecular weights of about 50 kD and about 70 kD, with a combined molecular weight of approximately 120 kD. SMC-TF is constitutively expressed in human vascular smooth muscle cells, and has a specific affinity for double-stranded nucleic acids containing the sequence 5'-GGGTTTTCCCC-3' (SEQ ID NO 2), and also other sequences in the rel-family of binding sites.

The two different subunits of the factor include a nucleic acid binding domain and a functional domain, although both subunits are required for binding and both may contain some functional activity.

SMC-TF represents a novel family of factors which is a subgroup of the rel-related factors. This novel family can be characterized by their affinity for common binding elements, a common molecular structure having at least two different subunits, and at least some common inhibitory and/or stimulatory properties. One of the subunits has a molecular weight of between about 45 kD to about 75 kD, or between about 50 kD to about 60 kD. The other subunit is between about 60 kD to about 80 kD, or between about 65 kD to about 75 kD. The complete structure has a molecular weight of between about 90 kD to about 150 kD, or between about 100 kD to about 130 kD. Binding to double-stranded nucleic acid typically requires the presence of both subunits. The more functional domain, generally the larger of the two subunits, regulates the expression of certain genes which may be directly or indirectly attributable to proliferation of the cells in which they are expressed.

SMC-TF regulates the proliferation of smooth muscle cells both in vivo and in vitro. Smooth muscle cell proliferation is directly involved with a number of diseases including arteriosclerosis, stenosis and restenosis, and various conditions and disorders related to fibrosis including fibrosarcomas, lymphomas and other neoplasms, fibroids of the uterus and other areas of the body, impotence, endocardial fibroelastosis and fibroadenomatosis of the breast. Additional fibroproliferative diseases which can be treated by compositions and methods of the invention include Crohn's disease (regional enteritis) and adult respiratory distress syndrome (ARDS). Crohn's disease is an inflammatory bowel disease that can involve all layers of the bowel wall. SMC proliferation results in fibrosis of the intestinal lumen and occlusion of the bowel. ARDS is brought on by insult or injury to the respiratory tract. Infiltration and hyperproliferation of SMCs occurs in the area of alveolar damage with a general fibrosis throughout the respiratory tract which can lead to severe and life-threatening respiratory failure.

Inhibition of SMC-TF activity decreases SMC proliferation and, consequently, ameliorates or overcomes these disorders. SMC proliferation can also be a useful characteristic. Tissues damage through injury or disease may include damage to SMCs or damage to cells which would directly or indirectly benefit by SMC proliferation. For example, SMC proliferation will promote the healing of damaged or diseased organs or muscles. Proliferation of SMCs and the expression of cytokines expressed by SMCs promote healing of the damaged areas.

SMC-TF and the SMC-TF-like factors can be purified using general and specific methods of purification. General methods include basic techniques for the isolation of protein from proteinaceous extracts as described in *Guide to Protein Purification* (M. P. Deutscher, editor, Methods in Enzymology, vol. 182, 1990). For example, individual proteins can be purified by techniques such as column chromatography, chemical extraction using, for example, ammonium sulfate, fractionation, high-pressure liquid chromatography (HPLC), reverse-phase-HPLC, fast-performance liquid chromatography (FPLC), or one- or two-dimensional gel electrophoresis. Specific techniques include affinity chromatography, antibody capture, excision and purification of protein bands following gel electrophoresis, western blotting techniques, and other fractionation procedures. Commonly employed methods of purification include separative techniques based on size, pI, hydrophobicity, solubility and selective adsorption.

A preferred method of purification involves preparation of cell-free extracts from surgically excised tissues or primary or continuous cultures of smooth muscle cells. Cells may be obtained from any mammalian source including humans. Extracts are prepared as described by Duyao et al. (M. P. Duyao et al., Proc. Natl. Acad. Sci. USA 87:4727–31, 1992). Protein concentrations of the extracts are determined using a Bradford or another similar assay. Extracts are diluted into an appropriate buffer and applied to an affinity column containing a matrix material conjugated with oligonucleotides containing the factor binding sequence. Alternatively, SMC-TF-specific antibodies can be bound to a matrix material such as sephadex, sepharose, sephacryl or another suitable resin. Fractions collected from the column are screened for the presence of SMC-TF using a functional assay for SMC-TF activity, such as sequence-specific binding, or a structural assay using monoclonal or polyclonal antibodies specific for the factor.

SMC-TF can also be produced recombinantly, for example, in eukaryotic or prokaryotic cells using standard, well-known techniques, many of which are described in *Current Protocols in Molecular Biology* (F. M. Ausubel et al., editors, John Wiley & Sons, New York, 1994). The genetic sequences which code for the subunits of SMC-TF are cloned, using methods known to those of ordinary skill in the art, into recombinant organisms. Recombinant prokaryotic cells which may be used include strains of *Escherichia*, *Bacillus* and *Streptomyces*. Recombinant eukaryotic microorganisms which are suitable for carrying and expressing the nucleic acid sequence of SMC-TF include mammalian and non-mammalian cells such as human, simian, murine, yeast and insect cell lines. The sequences or genes which encodes SMC-TF can be cloned into a vector appropriate to the cell type as may be necessary to achieve glycosylation or other eukaryotic-specific modifications of the protein. Plasmids, phage and cosmids are suitable for most bacterial cell lines. Viral and shuttle vectors may be used for eukaryotic cells and cell lines. The nucleic acid sequences which code for SMC-TF are determined using, for example PCR amplification of mRNA sequences isolated from SMC-TF expressing cells. Alternatively, the sequence may be isolated from a genomic or cDNA library, sequenced and cloned as desired using convenient restriction enzyme sites. Identification of the gene in a cDNA library is facilitated by using an expression library. Extracts from each member of the library are screened using, for example, anti-SMC-TF-specific antibodies or oligonucleotide probes containing a rel-specific binding sequence, until the clone or clones expressing the factor or portions of the factor can be identified. From these clones, the sequences of the SMC-TF genes and the sequences of untranslated regions of the genes can be determined.

The nucleic acid sequences determined may be cloned using well-known molecular biology techniques or may be synthetically constructed. Genes are incorporated into a vector such as a plasmid or viral vector containing all the necessary sequence information required for expression such as a strong and possibly regulatable promoter, transcription and translation initiation sites, splicing sites, if needed, and any necessary termination and polyadenylation sites. SMC-TF protein can be expressed in transformed prokaryotic or eukaryotic cells and purified. SMC-TF protein or protein fragments may also be synthetically constructed with synthetic and appropriately or otherwise modified amino acids using, for example, an automated peptide synthesizer.

Another embodiment of the invention is directed to compositions comprising SMC-TF or a SMC-TF-like factor, active fragments of these proteins or fusion proteins containing some portion of a factor, and a pharmaceutically acceptable carrier. Active fragments are those portions of the entire protein which have a substantial amount of the biological or physical activity of the entire protein or parts thereof. Appropriate carriers are determined by the route of administration of the factor and include water, oils, fatty acids, alcohols, salts, saccharides, polysaccharides, celluloses, starches and combinations of these carriers. Compositions may be prepared in a variety of formulations including tablets, coated tablets, capsules, granules, aerosols, syrups, emulsions, suspensions, solutions, and ointments with pharmaceutically acceptable excipients, solvents or slow release polymers and the like.

Another embodiment of the invention is directed to compositions containing agents which regulate the activity of SMC-TF or a SMC-TF-like factor. These compositions include antibodies, inhibitor proteins, cytokines, dominant negative mutations of, for example, p50, inhibitors of rel-like factors, anti-oxidants, natural or synthetic oligonucleotides, proteins or derivatives or combinations of these agents. For example, anti-sense oligonucleotides are useful to prevent transcription, processing and/or translation of the nucleic acid which encodes SMC-TF. Double-stranded oligonucleotides which contain the sequence of the binding site of SMC-TF may be used to compete the factor from its natural binding site. In either case, SMC-TF activity and smooth muscle cell proliferation are inhibited. SMC-TF activity may also be inhibited by certain cytokines or chemical agents such as IκB and anti-oxidants, preferably water soluble anti-oxidants, which directly inhibit SMC-TF activity. Other proteins which may regulate SMC-TF activity include IκB, IκB-α (MAD-3), IκB-β, IκB-γ, pp40, Bcl-3 and I-rel. These agents or fragments or combinations of these agents can be formulated into compositions as well.

Another embodiment of the invention is directed to methods for regulating the proliferation of smooth muscle cells. Proliferation is regulated by increasing or decreasing the functional activity of the smooth muscle cell transcription factor, SMC-TF or a SMC-TF-like factor. Regulation can be performed in vivo or in vitro. To increase the activity of SMC-TF, and thereby, increase the proliferation of SMCs, additional SMC-TF or agents known or suspected to increase SMC proliferation, may be added to SMCs. To decrease the activity of SMC-TF, agents which decrease SMC-TF expression, binding to nucleic acid or activity may be administered to SMCs. SMCs which are susceptible to treatments include mammalian cells and are preferably human smooth muscle cells.

Diseases which can be treated by controlling the proliferation of SMCs include benign and malignant smooth muscle cell neoplasms and other soft tissue tumors (fibromuscular dysplasia and hyperplasia), cardiovascular disorders such as arteriosclerosis, stenosis and restenosis, and various disorders associated with abnormal fibrosis. For example, cardiomyopathies associated with abnormal fibrotic changes include plaque formation of the vasculature, endocardial and endomyocardial fibrosis, fibroelastosis and fibrinous pericarditis. Common causes of these diseases include myocardial infarction, uremia, radiation to the chest, inflammation and inflammatory bowel diseases such as Crohn's disease, rheumatic fever, trauma and infections of viral or bacterial origin. Fibrinous disorders can occur throughout the body producing abnormal formation in the lungs, ovaries, kidneys, breast, uterus, liver and bone marrow. Even when benign, such formations can interfere with organ function and can present difficulties to the patient which may be life-threatening such as ARDS (adult respiratory distress syndrome) or merely problematic such as impotence. Fibrous bodies such as, for example, fibroids of the uterus can create serious physical complications, for example, during pregnancy and childbirth and also at other times. By regulating SMC proliferation, which may include SMC multiplication or the expression of products from SMCs such as enzymes, cytokines, collagen, elastin and prostaglandins, the pathological consequences of these disorders can be substantially ameliorated or overcome.

Regulation of cell proliferation includes control of metabolic events such as cell multiplication, entry into the S or G phases of the cell cycle, mitosis, replication, apoptosis, the activation or suppression of oncogenes and other regulatory gene products, adhesion, cAMP or p53 related functions, transcription and RNA processing, translation and the events associated with protein expression including the expression of secreted substances (e.g. enzymes, hormnones, extracellular matrix (ECM) proteins such as collagen, elastin and proteoglycans, cytokines and secreted cytokines, prostaglandins, SMC-TF). Although regulation of SMC proliferation is the preferred embodiment, regulation of the proliferation (cell division, cell cycle control, mitosis, protein expression, etc.) of other cells such as skeletal muscle cells, cardiac muscle cells and other types of cells is also contemplated, the touchstone being whether or not such cells express or are affected by SMC-TF or a SMC-TF-like factor. Agents which regulate factor activity can be used to treat or prevent all such diseases and disorders.

Inhibitory agents, stimulatory agents or the transcription factor itself may be prepared into formulations appropriate for administration to the cells or a patient. The patient may be a mammal and is preferably a human. Effective amounts for in vivo use are between about 1.0 ng/kg body weight to about 10 mg/kg body weight, preferably about 10 ng/kg to about 1.0 µg/kg, and more preferably between about 100 ng/kg to about 500 ng/kg. In some cases, such as where administration is local or site-directed, it may be desirable to use less than the above mentioned amounts, while in other cases additional active reagents will be preferred. Compositions may also be used to regulate SMC activity in vitro such as in cell culture for production of SMC products and for the use of expanded SMC populations in downstream procedures such as cell transplantations and infusions. Effective amounts for in vitro use are between about 1.0 nM to about 10 mM, preferably between about 10 nM to about 1.0 µM, and more preferably between about 100 nM to about 500 nM. A treatment is considered effective if smooth muscle cell proliferation, as measured by cell multiplication, DNA synthesis, RNA synthesis, or general or specific protein expression, is increased or decreased by at least about 20%, preferably at least about 50% and more preferably at least about 75% to about 90% or more. In certain cases it is possible to alter a measurable parameter of proliferation two-fold, preferably ten-fold, and more preferably many fold.

A variety of means of to inhibit the in vivo or cell culture proliferation of SMCs are available. For example, SMC-TF can be inhibited from binding to its target DNA binding element. This inhibition can be achieved either through binding functionally inactive protein fragments directly to the targeted sequence or by interaction of competing oligonucleotide sequences with the protein. Expression of SMC-TF can also be prevented or substantially inhibited with the use of anti-sense oligonucleotides. Such oligonucleotides have been demonstrated to bind to DNA and mRNA and specifically inhibit the processes of transcription, RNA processing and translation.

Oligonucleotides, as well as other agents, can also be introduced into cells in vivo. One method for the introduction of nucleic acid is through the use of expression vectors such as plasmids, phages, cosmids or viruses. Useful recombinant viruses include the herpes-type viruses (CMV, HSV, EBV), retroviruses (HIV), adenoviruses, poxviruses and influenza viruses. Briefly, a nucleic acid with the desired sequence is cloned into a recombinant vector with the appropriate signal sequences for expression in the desired host. The vector, for example, a recombinant adenovirus construct, is introduced to the host through natural or artificial infection. Alternatively, the virus may be transformed into host cells which are reintroduced or explanted into the host after transformation has been confirmed. Such methods include transfection such as liposome-mediated transfection, receptor-mediated endocytosis, transduction, cellular bombardment with microparticles or chemical or electrical uptake of nucleic acid. Oligonucleotides may also be directly injected into the desired cells. Stability of these oligonucleotide may be increased through the use of sulfur-containing deoxyribonucleotide analogs. For example, replacement of the phosphate linkage with a phosphorothioate greatly increases oligonucleotide stability to nuclease degradation.

Local or site-directed delivery of oligonucleotides or any agent can be performed by injection, pulmonary absorption, oral ingestion, topical application, macromolecular targeting using conjugates and fusion proteins, and immediate or coordinated release from implants. Useful implantable devises include catheters, stents or coated articles placed into the host. Continuous application can be achieved through the use of the selected formulations on the implants which delay the release or provide a timed-release of the agent. The activity of agents can be enhanced through binding to other molecules. For example, an oligonucleotide can be conjugated to a ligand which, when receptor bound, is endocytosed into the cell. Alternatively, oligonucleotides may be bound to vasodilators, anti-thrombogenic reagents and the like. SMC-TF activity may also be inhibited using anti-oxidants or reducing agents. Such reagents can be formulated and delivered either systemically or locally. SMC-TF activity can also be inhibited using inhibitor proteins or active portions or fragments of these proteins. Proteins which inhibit SMC-TF include IκB and its variants, IκB-α (MAD-3), IκB-β, IκB-γ, pp40, Bcl-3, the dominant negative p50 (I-rel), and various antibodies.

Macromolecules can be delivered locally by a variety of techniques. For example, proteins may be delivered, linked to conjugates which are taken up by the appropriate cells. Slow release of proteins from implants, injection, inhalation, charge modification and modifications which allow the protein to be targeted to a particular site. Additional techniques which may be used have been previously described or are known in the art.

Compositions may be combined with other pharmaceutical agents or treatments such as those known or suspected to affect cell proliferation to obtain additive or synergistic properties. Examples which may be useful to control SMC proliferation include anti-thrombogenic agents, anti-proliferative agents, vasodilators, β-blockers, calcium antagonists, nitric oxide (NO) donors, diuretics, adrenergic inhibitors, ACE inhibitors and the like. Accordingly, compositions may also be combined with other forms of therapeutic or prophylactic treatment regimens.

Dosage of these compositions may be titered according to functional consideration such as that dosage sufficient to achieve a desired biological effect. Treatment or prevention regimens may involve continuous administration such as by intravenous drip, or periodic such as by tablet or capsules taken at set periods each day. With this method, inhibition or reversal of a biological effect, such as for example stenosis or restenosis, can be accurately titered. It may be necessary to deviate from the amounts mentioned depending on the body weight, type and timing of administration, type of formulation, characteristics of the compounds used, and the severity of disease and side effects.

Preferably, the active component of the composition is present in a concentration of about 0.01% to about 90%, by weight, of the total mixture, and more preferably between about 1.0% to about 20% and even more preferably between about 2% to about 10%. Amounts may vary according to the route of administration. For example, an anti-oxidant may be administered orally whereas a protein or peptide is usually administered intravenously or locally. A variety of additives may be employed including emulsifiers, dispersants, suspending agents, disintegrators, lubricants and binders. Formulations may also include anti-oxidants, preservatives, stabilizers, diluents, buffering agents, moistening agents, flavoring agents and coloring agents. Choice of formulation may vary depending on other considerations including storage and transportation requirements. Some compositions may be light sensitive, while others have a short half-life or absorb to plastic. The choice of formulation will be determined accordingly. Furthermore, certain other compounds may be incompatible in a particular formulation necessitating the separate administration regiments.

Another embodiment of the invention is directed to methods for regulating the expression of proteins whose genes contain a binding element recognized by SMC-TF or SMC-TF-like factors. By regulating the activity of SMC-TF, the expression of a single gene or group of genes can be effectively controlled. This method can be used in vitro or in vivo in tissue culture or patients to control the expression of a specific gene. Genes which may be controllable include genes introduced to a patient for gene therapy and genes present in recombinant cells and vectors. The only requirement is that the controlling regions of the gene contain a SMC-TF or SMC-TF binding site. Such sites are found naturally in certain genes and can be introduced where desired using molecular biology techniques known to those of ordinary skill in the art.

Examples of genes whose expression can be regulated include genes which express ECM proteins such as laminin, collagen and fibronectin, adhesion molecules (the $\beta_2$-integrins such as LFA-1, MO-1 and p150/95, ICAM, VCAM), inflammatory mediators such as FMLP C3a and LPS, cytoskeletal proteins such as vinculin, talin and actin, recombinant proteins such as fusion proteins, other transcription factors and proteins involved with transcription, RNA processing or replication.

Another embodiment of the invention is directed to methods for regulating the proliferation of biological organisms. Regulatable organisms contain one or more genes which are directly or indirectly involved with proliferation that contain a controlling element recognized by SMC-TF or SMC-TF-like factors. By regulating the activity of the factor, proliferation of the organism can be effectively controlled. To regulate proliferation means to control, for example, cell multiplication, mitosis, adherence, entry into a phase of the cell cycle, secretion, chemotaxis, inter-cellular and intra-cellular signaling, replication, transcription, RNA and protein processing and other events associated with metabolic processes of the cell. Biological organisms which can be regulated include certain parasites, bacteria, and preferably, viruses. Regulatable viruses include the herpes family of viruses such as cytomegalovirus (CMV) and herpes simplex virus types 1 and 2, the retroviruses (e.g. enhancer sequences) such as the human immunodeficiency viruses (e.g. HIV-1), and selected human papilloma viruses (HPV). Control over the proliferation of viruses includes control over diseases which may be caused by the virus. Consequently, methods and compositions of the invention which regulate SMC-TF and SMC-TF-like activity may be used to treat or prevent these diseases and disorders.

The following experiments are offered to illustrate embodiments of the invention, and should not be viewed as limiting the scope of the invention.

EXAMPLES

Example 1
Cell Cultures.

Smooth muscle cell explants were obtained from the pulmonary arteries of female calves (M. A. Stepp et al., J. Biol. Chem. 261:6542–6547, 1986). Cells were grown to confluence in Dulbecco-Vogt minimal essential medium (DVMEM; J. R. H. Biosciences; Lenexa, Kans.) supplemented with 4 mM glutamine, 50 units/ml penicillin, 50 units streptomycin and 10% fetal bovine calf serum. Cells were rendered quiescent by growth to confluence, or passed via trypsinization in tissue culture. Second- and third-passage cells were used for experiments.

Example 2
Transfection Assays.

Cells were grown to between about 50% and about 80% confluence and fed with 10% FCS-DVMEM for 2 to 4 hours before transfection. CsCl$_2$-purified DNA (20 µg/p60 and 50 µg/p100) was transfected by the modified CaPO$_4$ transfection procedure of Chen et al. (C. Chen et al., Mol. Cell. Biol. 7:2745–55, 1987). To test the effects of serum stimulation, cultures were transfected in duplicate, switched to 0.5% FCS-DVMEM and incubated for 48 hours to allow cells to become quiescent. Fresh non-essential amino acids and sodium pyruvate were added to all cultures and to one set, FCS was added to 20%. All cultures were incubated for an additional 48 hours.

Cell lysates were prepared as described by Duyao et al. (M. P. Duyao et al., Proc. Natl. Acad. Sci. USA 87:4727–31, 1990). Lysates were characterized by protein concentration using the Bradford assay (Bio-Rad Laboratories; Hercules, Calif.). Equal amounts of lysates (20–100 µg) were incubated with acetyl CoA (Sigma Chemical; St. Louis, Mo.) and 2 µl [$^{14}$C]chloramphenicol at 57 Ci/mmol, 25 nCi/µl (Amersham; Arlington Heights, Ill.) in 0.25 M Tris-HCl, pH 8, for 4 hours at 37° C. and the products resolved on silica gel TLC plates (Whatman Laboratory Products; Clifton, N.J.) in chloroform: methanol (19:1). Following autoradiography, spots were cut from the plate and counted in Ecoscint scintillation cocktail (National Diagnostics). Alternatively, equal amounts of lysates were incubated in 2.5 µCi [$^3$H]acetyl CoA at 200 mCi/mmol (DuPont NEN Products; Boston, Mass.), 50 µM acetyl CoA, and 1.6mM chloramphenicol for 1–2 hours and the acetylated forms extracted with ethyl acetate and assayed by liquid scintillation counting.

Example 3
Preparation of Extracts: Mobility Shift Assays.

Nuclear extracts were prepared from SMCs as described by Dignam et al. (J. Dignam et al., Nucl. Acids. Res. 11:1475–1489, 1983). Murine B lymphoma WEHI 231 cells were cultured (M. P. Duyao et al., Proc. Natl. Acad. Sci. USA 87:4727–31, 1990), and nuclear extracts prepared as described by Strauss et al. (F. Strauss et al., Cell 37:889–901, 1984). Oligonucleotides were end labeled with Klenow and [α$^{32}$P] dNTPs.

The electrophoretic mobility-shift assay was performed as follows: Approximately 2 ng of labeled DNA (50,000 dpm) and 5 µg of nuclear extract were mixed with 5 µl of 10 mM Hepes, pH 7.5, 4 mM dithiothreitol (DTT), 0.5% Triton X-100 (TX-100), and 2.5% glycerol and adjusted to 10 µg of poly(dI-dC)/poly(dI-dC) co-polymer and 75 mM KCl in a final volume of 25–50 µl. This mixture was incubated for 30–45 minutes at room temperature, and DNA-protein complexes electrophoresed at 15 V/cm in a 5% polyacrylamide gel using TAE gel running buffer (40 mM Tris-base, 40 mM glacial acetic acid, 1 mM EDTA, pH 8). Where indicated, IκB-α-GST fusion protein (40 ng or 2 µg) was added to the binding reaction. Alternatively, 2 µg of antibody against the p50 homodimers (Santa Cruz Biotechnology; Santa Cruz, Calif.), was added 15 minutes after binding and the reaction was continued at room temperature for 30 minutes. A final incubation was performed at 4° C. for an additional 1.5 hours. Cognate peptide (0.4 µg; an approximate 25-fold amount per IgG antigen binding site) was added with the antibody to test for the specificity of the reaction.

Example 4
Oligonucleotides and Constructs.

Wild type and mutant oligonucleotides containing the NF-κB binding sequence derived from the URE from c-myc were obtained. Their sequences are as follows:

wild-type: 5'-GATCCAAGTCCGGGTTTTCCCCAACC-3' (SEQ ID NO 3)

mutant 1: 5'-GATCCAAGTCCGCCTTTTCCCCAACC-3' (SEQ ID NO 4)

mutant 2: 5'-GATCCAAGTCCGGGTTGGCCCCAACC-3' (SEQ ID NO 5)

mutant 3: 5'-GATCCAAGTCCGGGTTTTGGCCAACC-3' (SEQ ID NO 6)

mutant 4: 5'-GATCCAATGAAGGGTTTTCCCCAACC-3' (SEQ ID NO 7)

The core sequence of the NF-κB element is in bold font, and the mutated bases are underlined. Oligonucleotides corresponding to the wild-type and mutant 1 URE sequences were synthesized (Amber, Inc.; Guilford, Conn.) with directional Bam HI linkers and two copies were cloned into the Bam HI site of the thymidine kinase (TK) promoter CAT vector, in the sense (E8 or E8-mut) or anti-sense (E9 or E9-mut) directions (Duyao, M. P., et al. Proc. Natl. Acad. Sci. U.S.A. 87:4727–4731, 1990). The E8 and E9 vectors respond virtually identically to induction by phorbol ester, tax or IL-1 (Duyao, M. P., etal. Proc. Natl. Acad. Sci. U.S.A. 87:4727–4731, 1990; Duyao, M. P., et al. J. Biol. Chem. 267:16288–16291, 1992; Kessler, D. J. et al. J. Exp. Med. 176:787–792, 1992) and are used interchangeably. TK-CAT vectors containing two copies of the NF-κB element of the kappa light chain enhancer were also utilized. The HIV-LTR was cloned in either the sense or anti-sense orientation in front of the CAT-SV40 poly A (Hind II to Bam HI) fragment of the pSV2CAT vector (L. -J. Chang et al., J. Virol. 67:743–52, 1993). Either the three SP1 elements between −79 to −39 b.p. (dl.Sp1) or the two NF-κB elements within −129 to −79 b.p. were deleted (dl.kB). Expression vectors for wild type p50, p52 and p65 and a dominant negative p50 mutant which dimerizes, but fails to bind DNA (V. Bours et al., Mol. Cell. Biol. 12:685–95, 1990; P. Bressler et al., J. Virol. 67:288–93, 1993).

Example 5
C-myc Binding Element is Constitutively Activated in SMCs.

Figure 1B:
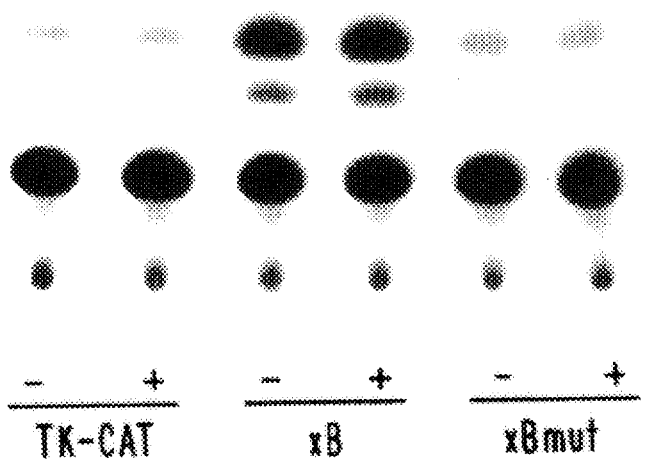

As an initial test of the ability of serum to activate c-myc transcription in SMCs through induction of NF-κB activity, a transfection analysis was performed using CAT reporter constructs in which a thymidine kinase (TK) promoter was driven by two copies of the NF-κB binding element from the c-myc gene. Cultures of SMCs were transfected with constructs driven by two copies of either the wild type URE (E8), mutant 1 URE element (E8-mut), or parental TK-CAT. Following incubation under serum deprivation conditions for 24 hours, cultures were stimulated for 24 hours with re-addition of serum. Equal amounts of lysates were prepared from serum deprived and stimulated cultures and assayed for CAT enzyme activity. Serum stimulated NIH-3T3 fibroblasts showed an increase of NF-κB mediated transcription in cells containing constructs driven by the wild type (E8) binding element, whereas no effect was seen with the E8-mut constructs (A. S. Baldwin et al., Mol. Cell. Biol. 11:4943-51, 1991). However, addition of serum had little effect on CAT activity in SMCs when CAT transcription was driven by the wild type URE (FIG. 1a). The basal level of CAT activity observed with the wild type E8 constructs was significantly higher in these cells than background CAT activity seen with the parental TK-CAT vector (FIG. 1b). This appeared specific for the NF-κB binding element since the E8-mut vector displayed very low activity, plus or minus serum. Similar results were obtained with cultures of SMCs derived from the carotid artery. A high level of a rel-related activity in SMCs was observed and this factor was named the smooth muscle cell transcription factor (SMC-TF).

Example 6
Characterization of the Binding Activity of SMC Nuclear Proteins to NF-κB Binding Elements.

Figure 2:
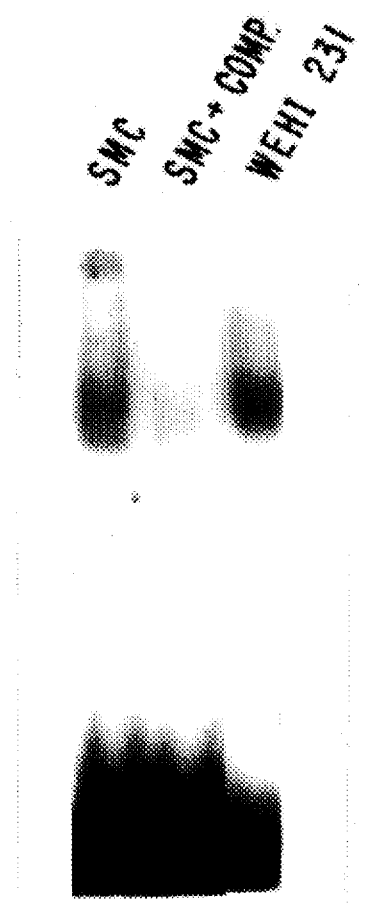
FIG. 2 SMCs express a factor that binds to an NF-κB binding element.

Mobility shift analyses were performed to characterize the nature of the SMC-TF binding to the NF-κB binding elements. The URE oligonucleotide was employed since this element is close to the consensus sequence and it has been shown to bind effectively to various members of the rel family (M. P. Duyao et al., Proc. Natl. Acad. Sci. USA 87:4727-31, 1990; F. La Rosa et al., Mol. Cell. Biol. 14:103944, 1994; D. J. Kessler et al., J. Exp. Med. 176:787-92, 1992). The electrophoretic mobility shift profiles obtained with nuclear extracts from SMCs were compared with those of the murine B cell line WEHI 231 (FIG. 2). Binding of WEHI 231 extracts to the URE has been shown to be due to rel-related factors, which are abundantly expressed in this cell line (R. Sen et al., Cell 47:921-28, 1992; M. P. Duyao et al., Proc. Natl. Acad. Sci. USA 87:4727-31, 1992; N. Rice et al., M. EMBO J. 12:4685-95, 1993; S. Miyamoto et al., Mol. Cell. Biol. 14:3276-82, 1994). The bands obtained with the bovine SMC extract migrated similarly to those of murine WEHI 231 cells, although the intensity of binding was lower. Competition with 50-fold molar excess of cold URE confirmed the specificity of this binding.

Figure 3:
FIG. 3 Electrophoretic mobility shift assay of URE-binding activity in nuclear extracts of human myometrium and human leiomyoma tissues.

Normal human uterine tissue (myometrium) and human uterine fibroid tissue (leiomyoma) surgically obtained were prepared by collagenase digestion. Nuclear extracts were prepared as described. Samples were incubated for 30-45 minutes at room temperature with double-stranded, end-labeled oligonucleotides representing the binding site sequence of SMC-TF (mutant 3) plus and minus cold competitor DNA (wt URE). DNA-protein complexes formed were electrophoresed into a 5% non-denaturing polyacrylamide gel in TAE buffer and subjected to autoradiography. As shown in FIG. 3, both normal and fibroid human uterine tissues contain an endogenous rel-like factor or family of factors. The multiple bands observed in each lane may represent the various members of the family of factors. Differences in the migration pattern observed between healthy and fibroid tissues may represent the various levels of expression.

Example 7
Mutation of the Binding Element Eliminates Complex Formation.

Prior methylation interference studies indicated that within the footprinted 5'-AAGTCCGGGTTTTCCCCAACC-3' (SEQ ID NO 3) URE sequence, the three G residues of the upper strand and the four G and four A residues of the lower strand of the core sequence (underlined) are critical for binding of rel-related factors within WEHI 231 nuclear extracts (M. P. Duyao et al., Proc. Natl. Acad. Sci. USA 87:4727-31, 1990). To evaluate whether the contact points of SMC-TF are similar, mobility shift analysis was performed with mutant URE oligonucleotides (mutants 1-4).

Figure 4A:
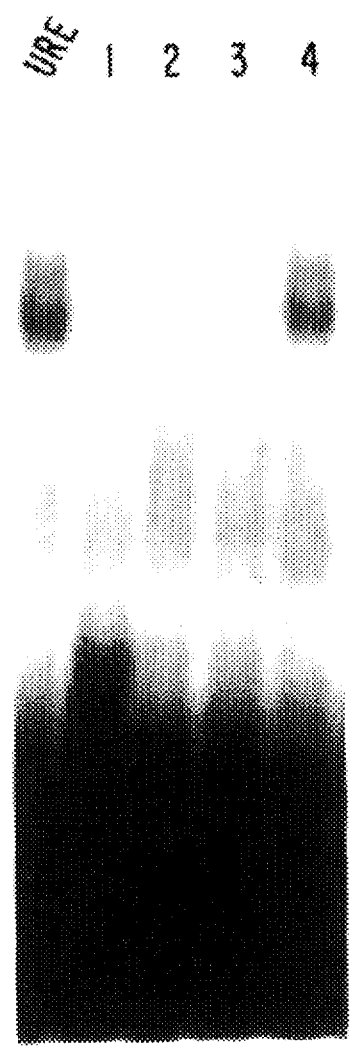
FIGS. 4A and B Mutation of the URE prevents binding of rel-related SMC factors in (a) SMC extracts and (b) WEHI 231 extracts.
Figure 4B:

As seen in FIG. 4a (lanes 1-3), mutation of either the internal two GG's (mutant 1), internal two TT's (mutant 2), or internal two CC's (mutant 3) prevented almost all SMC-TF binding. Similar results were obtained with a WEHI 231 nuclear extract (FIG. 4b). In contrast, a four base mutation upstream of the internal binding site (lane 4) only slightly reduced the binding of SMC-TF and WEHI 231 factors. Interaction of the URE with SMC-TF involves specific contact with bases at both the 5' and 3' halves of the internal NF-κB binding site of the oligonucleotide in a manner similar to that seen with rel-factors within nuclei of the B cell lymphoma WEHI 231.

Example 8
Inhibition of Complex Formation with Inhibitor Protein.

Figure 5:
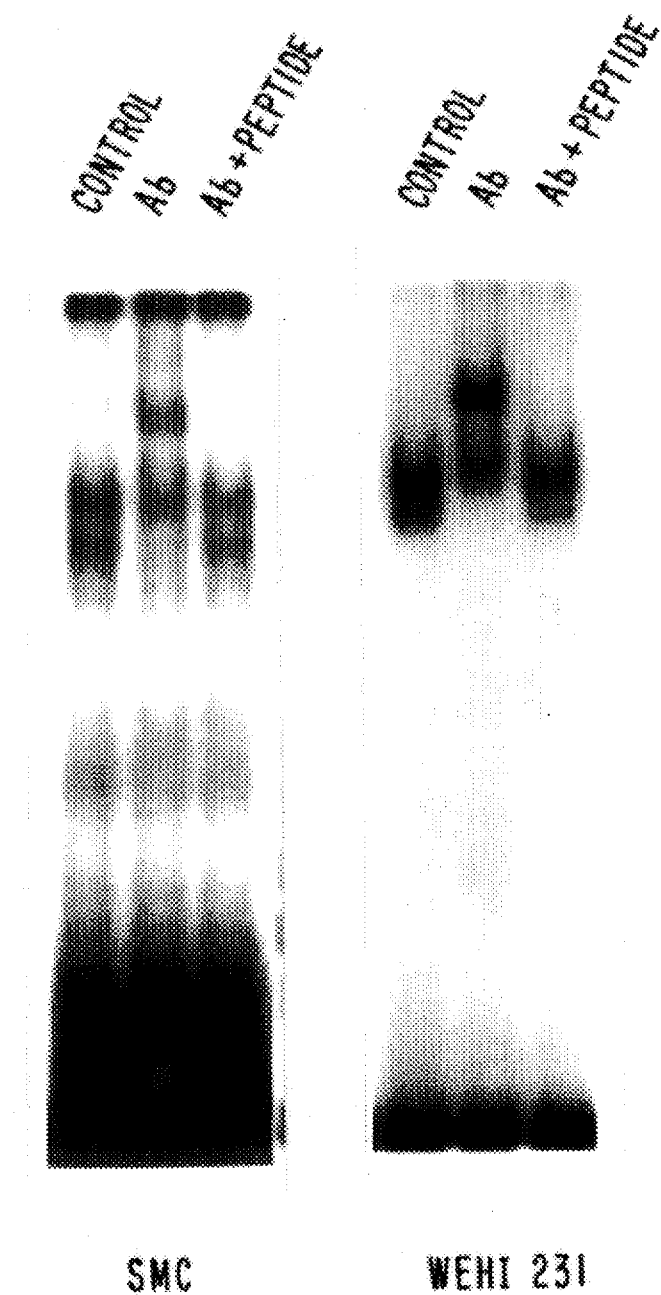
FIG. 5 Anti-p50 antisera specifically effects the rel-related factors/URE complex.

To identify which rel-related subunits might be present in the SMC-TF, antibody preparations against p50 homodimers, c-rel, rel B and p65 subunits were utilized. Addition of an antibody preparation that recognized p50 homodimers to reactions with either SMC or WEHI 231 nuclear extracts resulted in a specific supershift of the lower, more rapidly migrating band (FIG. 5). This supershift could be prevented by co-incubation of the antibody with the cognate peptide, indicating the specificity of the reaction. A slight shift of the upper complex was also observed in SMCs treated with the p50 antibody. Thus, the bottom complex contains the p50/p50 homodimer bound to the URE in both cell types and the upper complex apparently contains a p50 subunit as well.

Figure 6:
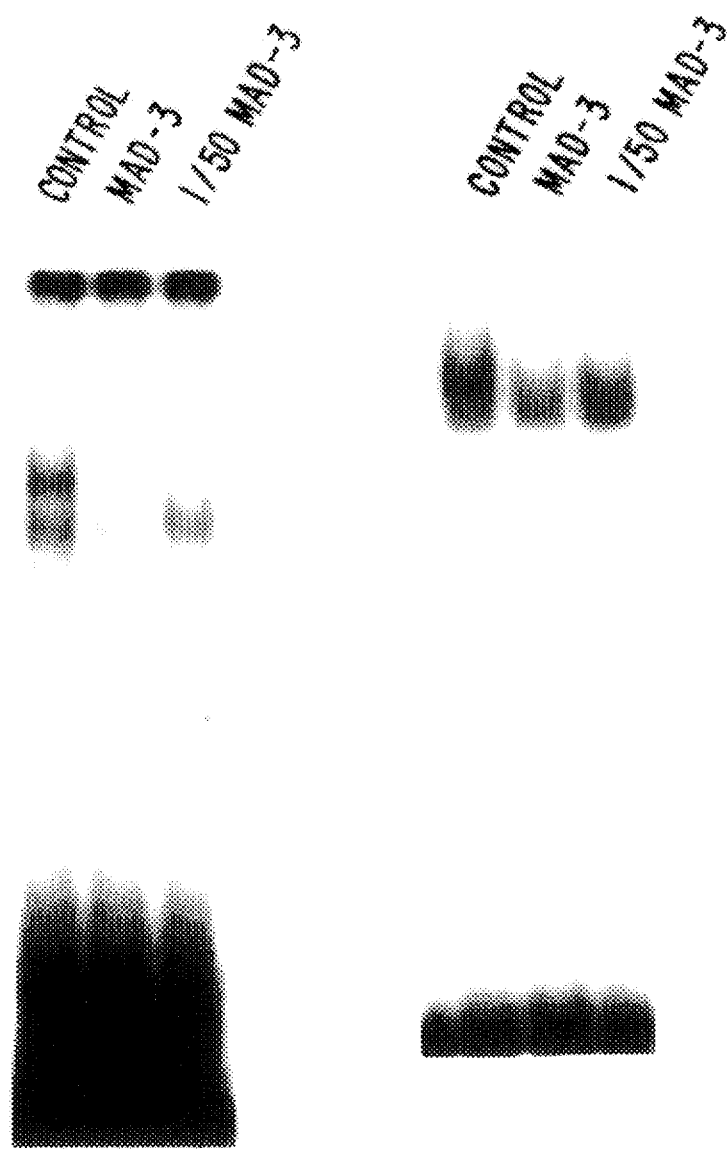
FIG. 6 IκB-α (MAD-3) inhibits formation of the rel-related factors/URE complex.

The inhibitor protein IκB-α, or MAD-3, has been shown to prevent rel-related factors from binding to DNA via selective interaction with the p65 or c-rel subunits. MAD-3 may also interact with the p50 subunit, however, inhibition of p50 homodimer binding requires a somewhat higher concentrations of inhibitor (Baeuerle, P. A. Biochem. Biophys. Acta 1072:63-80, 1991). Addition of low doses (1/50) of MAD-3 reduced the formation of the upper complex in both WEHI 231 and SMC extracts, while at higher doses there was a general reduction in formation of the bottom complex as well (FIG. 6). Thus the upper complex in SMCs contains a subunit that is inhibited by MAD-3.

To further identify the components of the upper complex, three antibody preparations against c-rel, two against p65 and one against p52 were used. All failed to shift bands in the SMC extracts, yet inhibited the formation of complexes in the WEHI 231 extracts. Furthermore, an antibody preparation against rel B failed to inhibit complex formation with either extract. These data are consistent with previous studies that demonstrated that the upper complex in WEHI 231 cells comprises mostly p50/c-rel, with some p50/p65 heterodimers, while the lower complex contains p50 homodimers (M. P. Duyao et al., Proc. Natl. Acad. Sci. USA 87:4727–31, 1990; N. Rice et al., EMBO J. 12:4685–95, 1993; S. Miyamoto et al., Mol. Cell. Biol. 14:3276–82, 1994).

Similar to WEHI 231 extracts, the lower complex in SMC extracts also contains p50 homodimers. The upper complex apparently contains a p50 subunit and a second rel-related factor that is inhibited by MAD-3. However, the second subunit does not appear to be c-rel, rel B or p65. It is known that the p50 homodimer is not able to activate certain promoters effectively in vivo. For example, p50 is unable to activate transcription of the c-myc promoter through its two NF-κB elements, whereas the p65 subunit was a potent transcriptional activator (F. La Rosa et al., Mol. Cell. Biol. 14:1039–44, 1994). Transcriptional activation observed is therefore the result of the higher molecular weight complex which is SMC-TF.

Example 9
Transfection Assays and Mobility Shift Experiments with Anti-oxidants.

Cells were grown to confluence, trypsinized, resuspended in medium plus 20% serum at a concentration of $20 \times 10^6$ cells per ml. A 0.8 ml sample of cell suspension was incubated on ice for 5 minutes. Cells were electroporated with 25 µg DNA at 300 V and 960 µF using a Biorad electroporater, returned to ice for 10 minutes, and plated at a density of $10^4$ cells per $cm^2$. After 24 hours, cells were harvested and assayed for CAT activity using a continuous fluor diffusion assay or betagalactosidase activity. Alternatively, cells were transfected by calcium phosphate method (C. Chen et al., Mol. Cell. Biol. 7:2745–55, 1987).

CMV constructs consisted of following: pON405 contains the intact murine CMV-α (immediate early) promoter sequences fused to a lac Z gene. The construct pON407 contains the same promoter, but with sequences 5' to –146 with respect to transcription start site deleted. The constructs pON407.18R3 and pON407.18T3 include the same sequences as pON407 and, in addition, three tandem copies of a synthetic 18-base pair repeat containing the CMV NF-κB sites in wild type or mutated forms, respectively.

Nuclear extracts were prepared by the miniprep procedure. URE double-stranded oligonucleotides containing the upstream NF-κB element of the murine c-myc gene. This fragment was end-labelled with $^{32}$P-γATP (DuPont NEN Products; Boston, Mass.) and T4 polynucleotide kinase (New England Biolabs; Beverly, Mass.) to specific activity 6000 Ci/mmol and purified by polyacrylamide electrophoresis. Nuclear extract (5 µg) was mixed with 10 µg poly(dI-dC) (Pharmacia Biotech; Piscataway, N.J.) and 25,000 dpm of labelled URE double-stranded oligonucleotide in 2 mM Hepes, pH 7.5, 1 mM DTT, 0.1% TX-100, 0.5% glycerol, and 100 mM KCl, in a volume of 25 µl and incubated at 23° C. for 30 minutes. DNA protein complexes were resolved by non-denaturing polyacrylamide electrophoresis in 4.5% acrylamide in a buffer of 0.022 mM Tris-borate, 0.5 mM EDTA.

Example 10
Determination of Cell Number in S Phase.

The number of cells traversing S-phase in a defined time period was determined by incubating cells in media containing $^3$H-thymidine (DuPont NEN Products; Boston, Mass.) at 2 µCi/ml. At the end of the labelling period, cultures were washed five times in phosphate buffered saline (PBS), fixed with methanol at –20° C. for five minutes, and air dried. Cells were overlayed with NT2B emulsion and exposed in the dark for five days. The emulsion was developed using Kodak D19 and Kodafix (Eastman Kodak; Rochester, N.Y.) as per manufacturer instructions, and counterstained, when desired, with Giemsa stain (Sigma Chemical; St. Louis, Mo.).

The number of cells undergoing DNA synthesis at different times after treatment with N-acetylcysteine (NAC) or pentoxifylline (PTX) was determined by labelling with $^3$H-thymidine and autoradiography. Twelve hour labelling windows were utilized at either 12–24 hours or 24–36 hours after treatment. NAC and PTX both inhibit SMC DNA synthesis in a dose-dependent manner as shown in Table 1.

TABLE 1

| Treatment | Percent Labeled Nuclei Hours Post-Treatment* | |
|---|---|---|
| | 12–24 | 24–36 |
| N-acetylcysteine | | |
| 0 | 85.9 | 69.8 |
| 2.5 mM | 41.0 | 48.3 |
| 5.0 mM | n.d. | 8.7 |
| 10 mM | 14.9 | 7.7 |
| 20 mM | 13.5 | 8.1 |
| Pentoxifylline | | |
| 0.625 mM | 65.5 | 66.8 |
| 1.25 mM | 28.8 | 45.3 |
| 2.5 mM | 22.1 | 38.8 |
| 5.0 mM | 9.9 | 10.0 |

(*= expressed as percent labeled nuclei)

Only 14.9% of cells underwent DNA synthesis 12–24 hours after treatment with 10 mM NAC and only 7.7% did so 24–36 hours after treatment. Only 9.9% of SMC treated with PTX at 5 mM traversed S phase after 12–24 hours after treatment. In contrast, vascular endothelial cells, which express no SMC-TF activity experience no inhibition of DNA synthesis at these doses. Thus, these two drugs which inhibit SMC-TF activity inhibit SMC proliferation.

Example 11
SMC Microinjection.

Exponentially growing SMCs on 100 mm tissue culture dishes were supplemented with 20 mM Hepes, pH 7.3, to maintain pH when exposed to open air. Grids approximately 4 $mm^2$ were drawn on the tissue culture side of the plates by hand with a 25 gauge needle. Cells were visualized on an unheated stage of an inverted Zeiss microscope situated on a vibration-free air table. Solutions for microinjection were adjusted to 100 mM KCl, 10 mM sodium phosphate, pH 7.3, and spun four successive times at 12,000×g for 5 minutes with subsequent transfer to new tubes at each centrifugation to eliminate particulates. Solutions were introduced into Eppendorf femtotip glass capillaries (1 µm tip diameter) using Eppendorf microloader tips. All cell nuclei in a defined grid were microinjected using a Narishige micromanipulator under conditions of constant flow under nitrogen pressure of 1.4 hPa at a rate of approximately 6–10 cells per minute. Successful microinjection was estimated to occur greater than 90% of the time. Following microinjection, the culture was washed with sterile PBS ten times to minimize potential contamination during microinjection, and returned to the incubator in normal medium. After 15 hours, cells were pulsed for 8 hours with $^3$H-thymidine and processed for autoradiography.

To confirm a direct role of SMC-TF activity in SMC proliferation, SMCs were microinjected with purified IκB-α, the naturally occurring inhibitor of NF-κB. Previous experiments had shown that the binding of the SMC-TF was prevented by the presence of this inhibitor. Exponentially growing SMCs were microinjected with IκB-α or as control bovine serum albumin (BSA) at concentration of 1 μg/μl. Assuming a microinjection volume of 10–11 ml and a molecular weight of 37 kD for this protein, it was estimated that approximately 150,000 molecules of IκB-α were introduced into the SMCs. Cells were labelled for 8 hours with $^3$H-thymidine for 16 hours after microinjection and processed for autoradiography. Duplicate experiments were performed with results shown in Tables 2 and 3.

TABLE 2

| Solution | Labeled Nuclei/Total Cells | Labeled Nuclei |
|---|---|---|
| None | 89/173 | 51.4% |
| Buffer | 102/213 | 47.9% |
| BSA, 1 μg/μl | 63/119 | 52.9% |
| IκB, 1 μg/μl | 26/141 | 18.4% |

TABLE 3

| Solution | Labeled Nuclei/Total Cells | Labeled Nuclei |
|---|---|---|
| None | 50/94 | 53.1% |
| Buffer | 59/113 | 52.2% |
| BSA, 1 μg/μg | 43/89 | 48.3% |
| IκB, 1 μg/μl | 7157 | 12.3% |

As shown, microinjection of IκB-α produced a strong inhibition of DNA synthesis. In contrast, microinjection of buffer alone or BSA did not inhibit DNA synthesis. Therefore the presence of IκB-α, the SMC-TF binding specific inhibitor, inhibits SMC proliferation.

SMCs were microinjected with the dsURE, or a dsURE mutant into at a concentration of 1 μg/μl. It was estimated that this would introduce 450,000 copies of the competitor into the cells. Twenty-four 24 hours after microinjection with URE, but not UREmut, far fewer cells could be seen in the microinjected area. Injection with buffer alone exerted no such effect. URE oligos inhibit in vivo SMC proliferation in a manner similar to IκB-α or the drugs NAC and PTX indicating that the SMC-TF activity is essential for SMC replication.

Example 12
SMC-TF Regulates the CMV Immediate Early Promoter.

Figure 7:
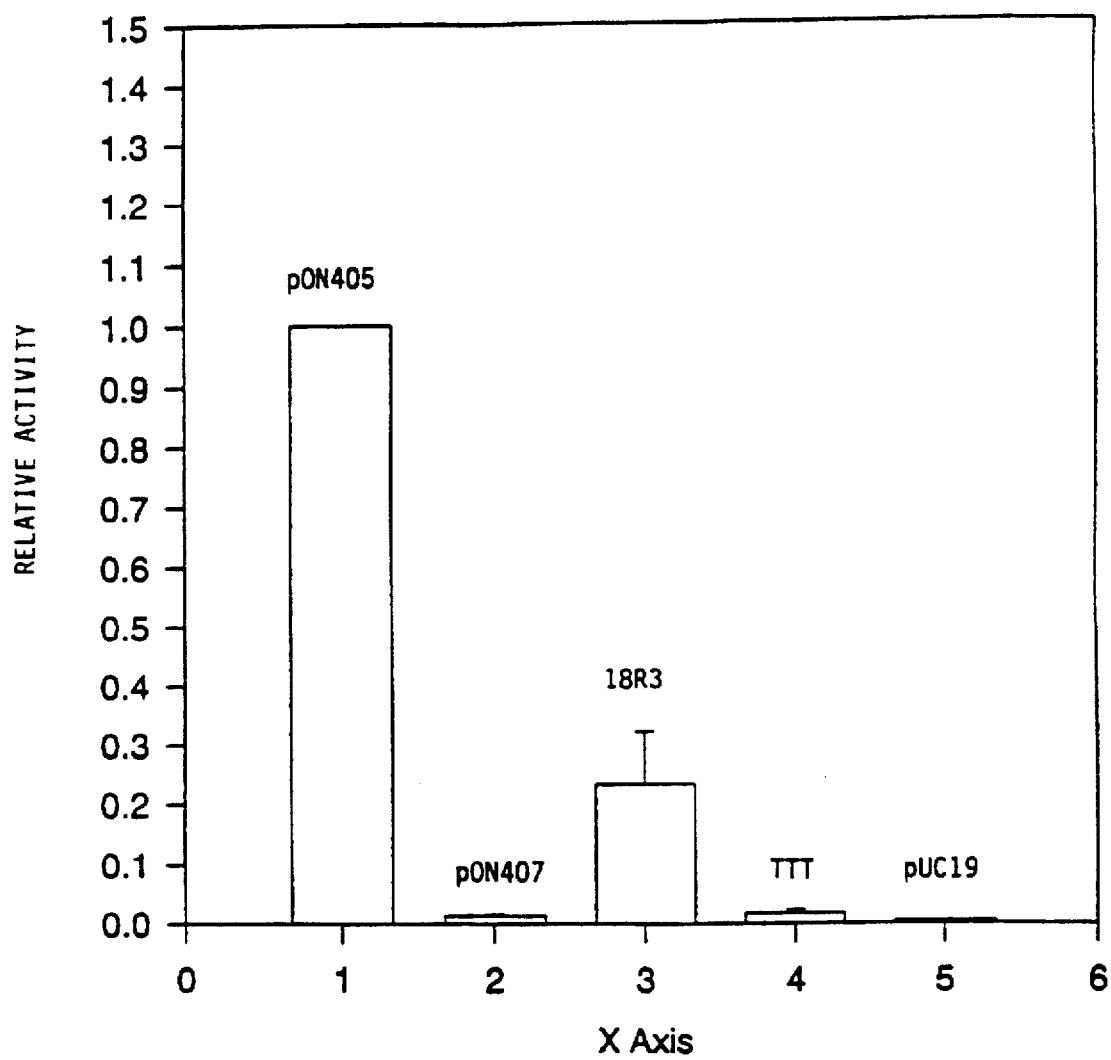
FIG. 7 SMC-TF activates the CMV IE promoter.

To determine whether SMC-TF affects the CMV immediate early (IE) promoter, transient transfection analysis was performed using CMV promoter-lac Z reporter constructs. The full length CMV IE promoter (pON405) was very active in SMC as shown in FIG. 7 (numbers shown indicate the mean of two separate plates with standard deviations of less than 15% of the mean). pON407, which deletes much of the promoter including the three copies of the NF-κB sites had thirty fold lower activity. pON407.18R3, which contains three tandem copies of the NF-κB sites, has ten-fold higher activity than pON407; however, pON407.18T3, which adds three mutant tandem copies of the NF-κB sites, has levels indistinguishable from pON407. In contrast, the pON407.18R3 promoter only gives high activity in T cells when the cells are activated upon treatment with phytohemagglutinin and phorbol ester to induce expression of NF-κB levels. This data suggests that SMC-TF activates the CMV promoter through its NF-κB sites.

Example 13
NAC Inhibits Inducible NF-κB Activity and Lowers Basal SMC-TF Activity.

Figure 8:
FIG. 8 NAC down regulates basal SMC-TF activity.

It was next determined whether known inhibitors of inducible NF-κB activity might interfere with SMC-TF activity and be of potential use in preventing CMV IE promoter activity. The anti-oxidant NAC blocks the induction of NF-κB (F. J. T. Staal et al., Proc. Natl. Acad. Sci. USA 87:9943–47, 1990). To determine whether NAC lowers the levels of SMC-TF activity in SMCs, electrophoretic mobility shift analysis was performed using double-stranded oligonucleotides corresponding to the upstream NF-κB site (URE) from the murine c-myc gene (FIG. 8). Quiescent SMC, which express levels of SMC-TF indistinguishable from exponentially growing SMCs, were treated for 24 hours with NAC at either 0 or 15 mM. To test for inhibition of induction of NF-κB, some cell cultures were administered IL-I or IL-6 for 1 hour, and nuclear extracts prepared (FIG. 8; lanes 3, 4 and 6–7). Cells represented in lanes 3 and 6 were treated with IL-1 at 10 ng/ml. Cells represented in lanes 4 and 7 were treated with IL-6 at 10 ng/ml.

Both IL-1 and IL-6 induced NF-κB activity in SMC. NAC treatment significantly lowered the basal levels of URE binding activity (lanes 2 and 5) and also the levels of activity obtained after treatment with IL-1. NAC did not effect the inducible level obtained by treatment with IL-6, suggesting that the mechanism of activation may not be sensitive to anti-oxidants. Similar inhibition was seen with nuclear extracts prepared from carotid artery SMC treated with NAC or PTX, another drug known to block inducible NF-κB activity. These data confirm that NAC lowers basal SMC-TF activity and inducible levels of NF-κB activity.

Example 14
NAC and PTX Inhibit SMC-TF Activity as Determined by Functional Assays.

Transient transfection assays were performed to test the effects of NAC and PTX on the functional activity of SMC-TF. A reporter construct carrying a chloramphenicol acetyl transferase (CAT) gene under the control of a basal herpes simplex virus thymidine kinase promoter with two copies of the URE, or two copies of a mutant URE that does not bind NF-κB/rel proteins (UREmut), were transfected by electroporation into either untreated SMCs or following pretreatment with NAC or PTX for 24 hours. As a control, a CAT gene under the control of the Moloney Murine Leukemia virus long terminal repeat (MoECAT) was similarly transfected. Twenty-four hours after transfection cell lysates were prepared and assayed for CAT activity (Table 4).

TABLE 4

| | Reporter Construct | | |
|---|---|---|---|
| Treatment | MoECAT | URE-tkCAT | UREmut-tkCAT |
| None | 20.9 ± 0.35* | 9.60 ± 0.31* | 1.95 ± 0.09* |
| NAC 20 mM | 24.6 ± 1.40* | 2.90 ± 0.45* | 1.90 ± 0.07* |
| PTX 2.5 mM | 25.4 ± 0.13* | 4.00 ± 0.22* | 2.34 ± 0.11* |

URE-tk CAT exhibits approximately five-fold higher activity than UREmut-tk CAT in untreated cells, confirming the presence of a SMC-TF activity. Pretreatment of the cells with NAC and PTX down regulated URE-tk CAT, but not UREmut-tk CAT or MoECAT, which is driven by other transcription factors. Thus, NAC and PTX inhibit the SMC-TF activity.

Example 15
Two Inhibitors of Inducible NF-κB Abrogate SMC Proliferation.

Figure 9B:
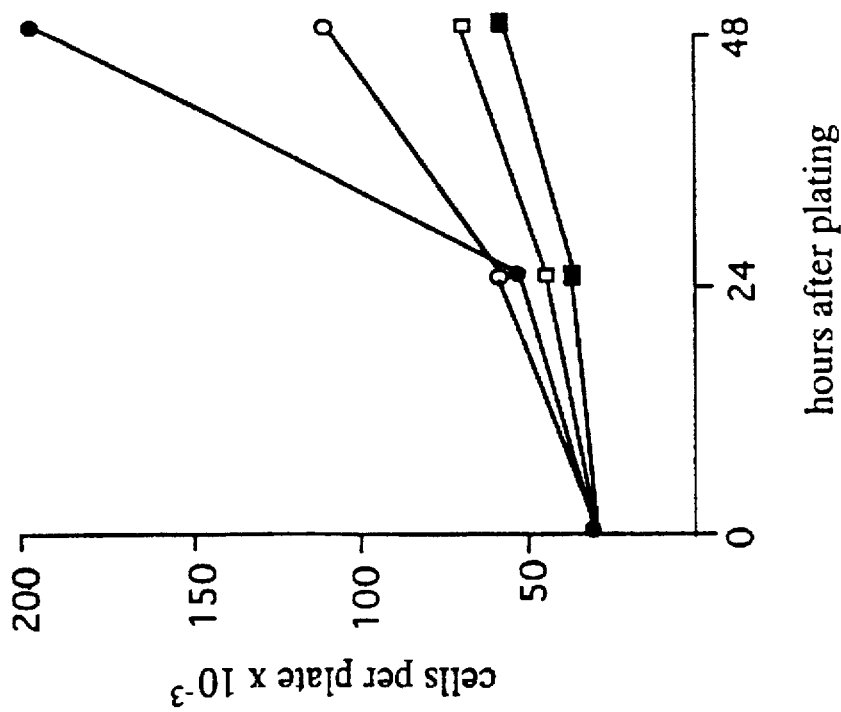
FIGS. 9A and B Cell counts after pretreatment with (a) PTX or (b) NAC, demonstrating that both PTX and NAC inhibit SMC proliferation.
Figure 9A:
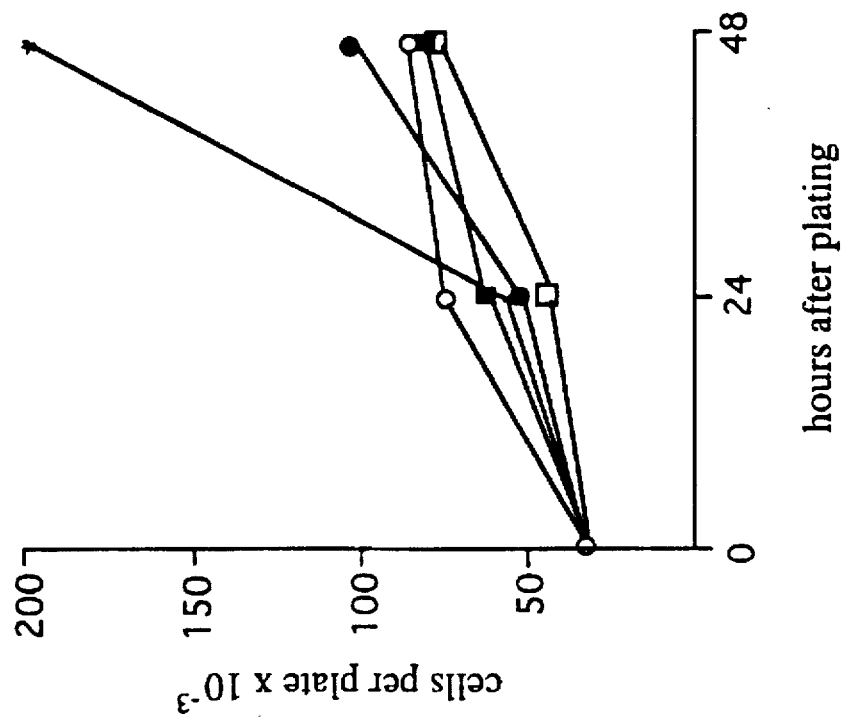

Exponentially growing SMCs were treated with various dosages of NAC or PTX. After 24 or 48 hours, cell numbers determined. Both NAC and PTX have no effect on cell viability as shown in Table 5 (numbers shown are the mean of two separate plates with standard deviations less than 5% of the mean), but potently inhibit SMC growth in a dose-dependent way as graphically depicted in FIG. 9 ((a) PTX; asterisk=0 mM, open circles=0.2 mM, closed circles=0.5 mM, closed squares=1.0 mM, open squares=2.5 mM; or (b) NAC; closed circles=0 mM, open circles 3 mM, open squares=10 mM, closed squares=30 mM).

TABLE 5

| Treatment | Hours After Treatment* | |
|---|---|---|
| | 24 | 48 |
| N-acetylcysteine | | |
| 0 | 92.7 | 97.3 |
| 3 mM | 91.3 | 97.1 |
| 10 mM | 93.7 | 95.6 |
| 30 mM | 92.1 | 93.7 |
| Pentoxifylline | | |
| 0.2 mM | 93.7 | 83.3 |
| 0.5 mM | 96.7 | 96.3 |
| 1.0 mM | 92.1 | 96.9 |
| 2.5 mM | 92.0 | 96.1 |

(*= percent of cells excluding trypan blue)

Cultures treated with either 10 mM NAC or 2.5 mM PTX for 48 hours are less than 30% the number of untreated cultures. Viability, as determined by trypan blue exclusion, is not decreased, and thus, the effects noted are not due to toxicity. Further, cells maintained in these drugs for 5 days resume growth when returned to normal medium. These effects are not seen in vascular endothelial cells, which do not express SMC-TF activity.

Example 16
Transcriptional Activation Modulated by Expression of Rel-Related Factors.

Figure 10:
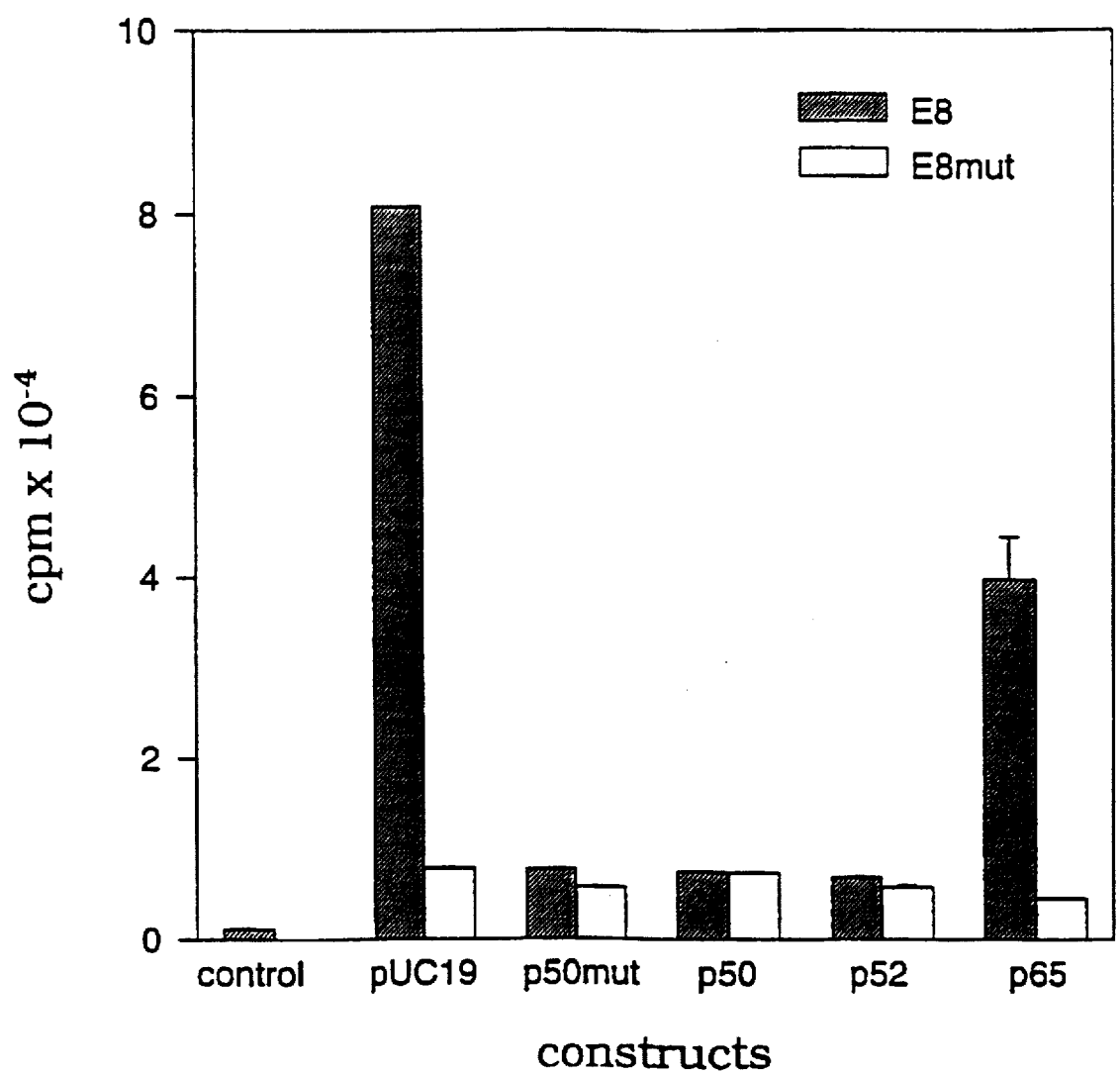
FIG. 10 Effects of expression of a dominant negative p50, wild type p50, p52, or p65 subunits on rel-related SMC activity.

To confirm that the transcriptional activation observed above was mediated through rel-related binding, the effect of a vector expressing a dominant negative p50 mutant was measured. The mutant p50 inhibits transcriptional activation by rel-related factors since it can interact with the various rel-related subunits but cannot bind to DNA (P. Bressler et al., J. Virol. 67:288–93, 1993). Expression of the mutant p50 dramatically reduced CAT activity of E8 (2 copy URE driven TK-CAT vector) upon co-transfection, but had no effect on the E8-mut (FIG. 10). These results suggest that the observed transcriptional activation is mediated by the binding of a rel-related factor and SMC-TF is rel-related.

The p50 and p52 subunits of NF-κB can bind the consensus sequence with great affinity, but do not contain strong transcription activation domains. Thus, they can serve as competitive inhibitors of complex formation. Co-transfection of E8 with vectors expressing either the p50 or p52 subunits led to a significant decrease in level of transcriptional activation as determined by CAT activity (FIG. 10). Activity of the E8-mut was unaffected.

The p65 subunit of NF-κB is a potent activator of the URE driven TK-CAT constructs in 3T3 fibroblasts, which contain only low levels of active rel-related factors (F. La Rosa et al., Mol. Cell. Biol. 14:1039–44, 1994). If the SMCs contain a constitutive NF-κB-like or rel-related activity, then the effects of p65 will depend upon the level, binding avidity and transcription activation potential of the endogenous factor. When a p65 expression vector was co-transfected with E8 at a 3-to-1 ratio, a drop in activity was noted (FIG. 10). The E8-mut was not induced by expression of p65. Failure of p65 to induce the overall transcription activity of the URE is consistent with prior expression of an active factor. The activity of the SMC-TF driving the URE element can be affected by over expression of other members of the rel-family of factors.

Example 17
SMC-TF Mediates Transcriptional Activation of the HIV LTR.

Figure 11:
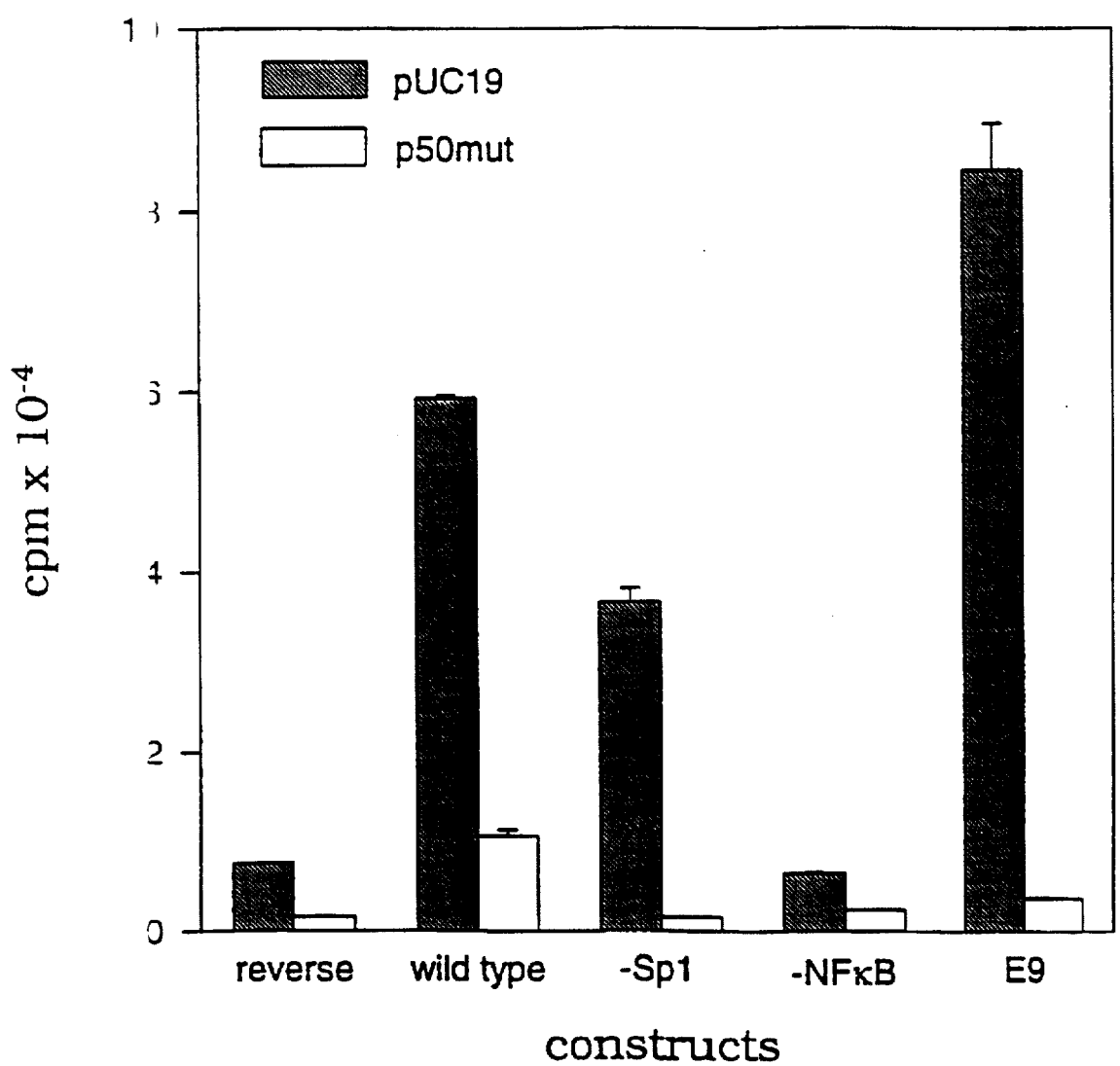
FIG. 11 Activity of the HIV-LTR in SMC cultures.

To assess the ability of SMC-TF to activate transcription of a homologous promoter through its own NF-κB binding elements, transfection analysis was performed with the HIV-1 LTR. The promoter of the HIV-1 virus is contained within the LTR region, and is driven by elements for the two factors NF-κB and Sp1 (L. -J. Chang et al., J. Virol. 67:743–52, 1993). Constructs in which the wild type LTR was placed in the correct or reverse orientations were used in transfection analysis into the pulmonary artery SMC (FIG. 11). The vector with the LTR in the forward orientation gave significant levels of activity. The level of activity was approximately 70% that of the two copy URE-TK-CAT E9 construct. In contrast, the reverse orientation HIV-LTR had only minimal activity, as expected.

Constructs in which either the two NF-κB or three Sp1 elements were deleted from the wild type HIV-LTR-CAT construct were similarly tested to determine the contribution of binding of each factor independently to the overall activity (FIG. 11). Deletion of the two NF-κB elements resulted in very significant loss of activity. Deletion of the Sp1 elements reduced the activity of the LTR, but to a lesser extent. The results of three similar transfections, indicate that removal of the two NF-κB sites reduces overall activity by approximately 83% (±14%). These results indicate that binding of the SMC-TF plays a major role in overall transcriptional activity of the HIV-LTR in smooth muscle cells.

Figure 12:
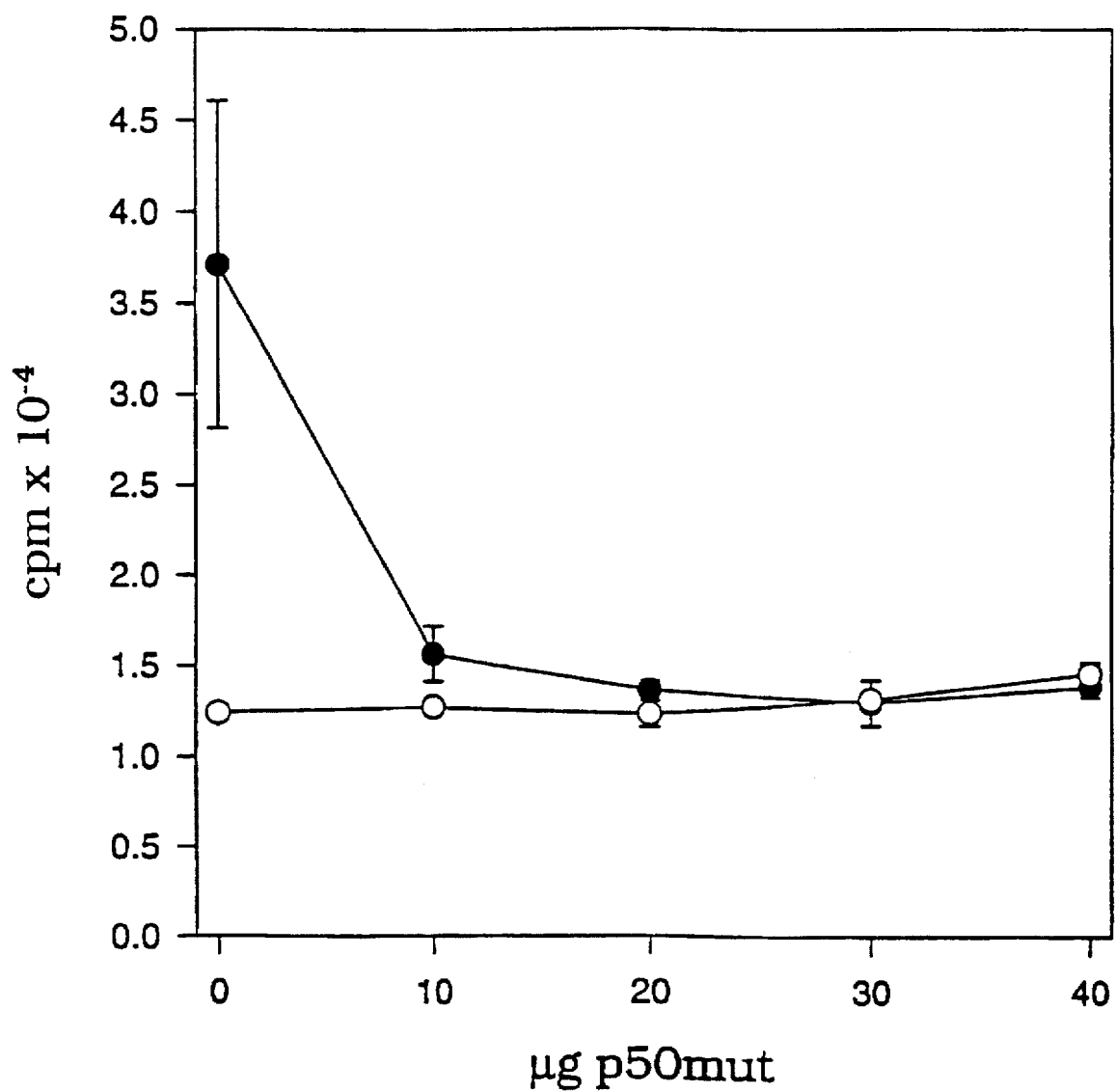
FIG. 12 Effect of the dominant negative p50 on expression of the HIV-LTR in SMCs.

To confirm the role of SMC-TF binding to NF-κB binding elements in SMCs, co-transfection analysis was performed with the mutant p50 expression vector (FIG. 11). The activity of the wild type and Sp1 deleted LTR were dramatically reduced by the expression of the dominant negative p50 subunit. A similar level of inhibition was seen with the wild type 2 copy URE-TK-CAT E9 vector. In contrast, the activity of LTR with the NF-κB elements deleted was only modestly affected. Titration of the effects of the dominant negative p50 indicate that the level of activity of the wild type LTR is reduced to that of the LTR with deleted NF-κB elements (FIG. 12). These results indicate that DNA binding of the SMC-TF plays a significant role in observed high level of activity of the HIV-LTR in smooth muscle cells.

Transfection and mobility shift analysis demonstrate that vascular smooth muscle cells contain a constitutive rel-related activity called SMC-TF. The activity was functional in activating the transcription of the HIV-1 LTR and the chimeric TK promoter driven by multiple NF-κB elements. Expression of a dominant negative p50 mutant inhibited the activity within SMCs. Furthermore, activity could be prevented by either mutation of the DNA element at sites known to mediate interaction with rel-related proteins, or addition of the MAD-3 inhibitor protein.

The bottom complex formed with the URE in SMC nuclear extracts appears to consist of a homodimer of p50. The upper complex is likely to contain p50 as a heterodimer with a second rel-related member. Low doses of MAD-3 prevented formation of this band, however, antibodies against p65, c-rel, and rel B had no effect on the formation of this complex. Since p50 homodimers do not activate transcription, the upper complex is believed to contain functionally active SMC-TF.

Example 18
Characterization of SMC-TF.

SMC-TF was purified from human SMC extracts prepared as described by Duyao et al. (M. P. Duyao et al. Proc. Natl. Acad. Sci. USA 87:4727–31, 1992). Briefly, extracts were tested for binding activity to an oligonucleotide containing the binding site sequence, and positive fractions subjected to sodium dodecylsulfate polyacrylamide gel electrophoresis (SDS-PAGE). The bands formed corresponded to two different subunits of about 50 kD and about 70 kD, with a combined molecular weight of approximately 120 kD when compared to other complexes formed with other members of the rel-family similarly analyzed.

Example 19
Cloning of SMC-TF.

Two different approaches are utilized to clone the genes which encode the subunits of SMC-TF. First, a human aorta lamda gt11 expression library is screened with $^{32}$P-radiolabeled p50 as described by LeClair et al. (K. P. LeClair et al., Proc. Natl. Acad. Sci. USA 89:8145–49, 1992). Positive plaques are purified and recombinant inserts isolated and sequenced. Alternatively, SMC-TF can be cloned by exploiting its homology with other of the rel-family of proteins. A human aorta lamda gt 11 expression library is screened with a probe derived by degenerate oligonucleotide-primed polymerase chain reaction (PCR) amplification of a domain highly conserved among members of the rel-family of factors as described by Sif et al. (S. Sif and T. D. Gilmore, J. Virol. 67:7612–17, 1993).

Example 20
Regulation of SMC Proliferation.

The effects of various agents are tested against SMCs in vitro. Briefly, SMCs obtained from calves or humans are maintained under tissue culture conditions (37° C., 5% $CO_2$, high humidity). Cells are divided into 100 mm tissue culture dishes at about $10^5$ cells per plate in 10% FCS/DMEM. To each plate is added the anti-oxidant NAC at 10 mM, the anti-oxidant PTX at 2.5 mM, or PBS as a control. To another set of similar plates, 25 ng wild-type or mutant-1 double-strand oligonucleotide is introduced to the cells by lipofectin transfection. All sets of plates receive $^3$H-thymidine for metabolic labeling. After 24 hours, all plates are scraped and the number of cells recovered counted. With the SMC-TF inhibitors NAC and PTX, and the binding-site oligonucleotide, SMC number is reduced compared to control samples. The total amount of thymidine incorporation which occurs in the $^3$H-labeled samples is determined by TCA precipitation. With SMC-TF inhibitors, total thymidine incorporation is reduced compared to control samples. Similar experiments are conducted using eukaryotic expression vectors which express either the SMC-TF protein or an irrelevant protein such as CAT protein as a control. In this case, cell number and the amount of $^3$H-thymidine incorporation are increased in the presence of vectors expressing SMC-TF protein.

Example 21
In Vivo Repair of Balloon Injured Arteries.

Balloon injury to the left common carotid arteries of male white rabbits is performed in three passes from an inflated 2F Fogarty balloon catheter (Clowes et al., Lab. Invest. 49:208–15, 1983). Animals are anesthetized with ketamine and rompun, and the catheter introduced into the left common carotid through a nick created in the external carotid artery. After removal of the catheter, the nick is tied off to prevent bleeding and promote healing. A minipump is implanted subcutaneously into the rabbits which, at a rate of 5 ng/hour, continuously administers compositions containing SMC-TF protein, IκB protein, I-rel protein or bovine serum albumin. Animal are fed a high cholesterol diet for fourteen days while being infused to promote SMC activity. After thirty days, animals are sacrificed and their aortas removed and analyzed. Upon microscopic examination, SMC proliferation shows a decrease in aortas which receive IκB protein or I-rel protein, and an increase in aortas which receive SMC-TF protein as compared to controls.

Example 22
Wound Healing with SMC-TF Ointment.

An ointment composition is prepared containing SMC-TF at about 0.01% of the composition by weight. The remaining components of the ointment include petrolatum and a stabilizing agent. A series of ¼ inch incisions are made into the epidermis of the forearms of four healthy, adult volunteers. A small amount of ointment is applied to half of the incisions. Half of the treated incision and half of the untreated incision are covered with a dressing. Healing is monitored for a total time period of about two weeks. Treated incisions heal in a shorter period of time than untreated incisions for both dressed and open wounds.

Example 23
Test of Anti-oxidants for the Treatment of Human Fibroids.

Ten healthy adult women volunteers between the ages of 30 and 37 with detectable fibroids of the uterus are selected based on stability of fibroid size for a four week period immediately preceeding the experiment. Volunteers are divided into two groups of five. Fibroid size is determined prior to the initiation of treatment. One volunteer from each group is given a dose of either NAC (0 mg, ½ mg, 1 mg, 2 mg and 5 mg) or PTX (0 mg, ½ mg, 1 mg, 2 mg and 5 mg) daily for two weeks. After two weeks, each is evaluated for an alteration of fibroid size. Both NAC and PTX reduce fibroid size when administered at all dosages of over ½ mg per day as compared to untreated controls.

Other embodiments and uses of the invention will be apparent to those skilled in the art from consideration of the specification and practice of the invention disclosed herein. The specification and examples should be considered exemplary only with the true scope and spirit of the invention indicated by the following claims.

We claim:

1. A purified transcription factor wherein said factor is comprised of two subunits of 50 and 70 kD that have a combined molecular weight of 120 kD wherein neither subunit is c-rel, rel B, or p65, and said factor specifically binds to a double-stranded nucleic acid containing the sequence 5'-GGGTTTTCCCC-3' (SEQ ID NO 2).

2. The factor of claim 1 wherein said factor regulates the proliferation of smooth muscle cells.

3. The factor of claim 1 wherein said factor is constitutively expressed in smooth muscle cells.

4. The factor of claim 1 wherein said factor binds only to double-stranded nucleic acids.

5. A composition comprising the factor of claim 1.

6. The composition of claim 5 further comprising a pharmaceutically acceptable carrier selected from the group consisting of water, oils, fatty acids, alcohols, salts, saccharides, polysaccharides, celluloses, starches and combinations thereof.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GGGACTTTCC                                                                                                    10

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GGGTTTCCC C                                                                                           11

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GATCCAAGTC CGGGTTTTCC CCAACC                                     26

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

```
GATCCAAGTC CGCCTTTTCC CCAACC                                              26
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

```
GATCCAAGTC CGGGTTGGCC CCAACC                                              26
```

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

```
GATCCAAGTC CGGGTTTTGG CCAACC                                              26
```

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

```
GATCCAATGA AGGGTTTTCC CCAACC                                              26
```